(12) United States Patent
Sheldon et al.

(10) Patent No.: US 8,876,881 B2
(45) Date of Patent: Nov. 4, 2014

(54) DEVICES FOR STENT ADVANCEMENT

(75) Inventors: Jeffery Sheldon, League City, TX (US); Richard Booth, Friendswood, TX (US); Gary Boseck, Boxford, MA (US); Richard Wisdom, Hydepark, MA (US); Ken Bueche, Friendswood, TX (US); Bruce Dannecker, Tyler, TX (US)

(73) Assignee: IDev Technologies, Inc., Webster, TX (US)

( * ) Notice: Subject to any disclaimer, the term of this patent is extended or adjusted under 35 U.S.C. 154(b) by 1625 days.

(21) Appl. No.: 11/876,764

(22) Filed: Oct. 22, 2007

(65) Prior Publication Data

US 2008/0097572 A1 Apr. 24, 2008

Related U.S. Application Data

(60) Provisional application No. 60/862,456, filed on Oct. 22, 2006.

(51) Int. Cl.
| | |
|---|---|
| *A61F 2/06* | (2013.01) |
| *A61F 2/966* | (2013.01) |
| *A61F 2/856* | (2013.01) |
| *A61F 2/95* | (2013.01) |
| *A61F 2/90* | (2013.01) |
| *B23K 26/20* | (2014.01) |
| *A61F 2/954* | (2013.01) |
| *A61F 2/962* | (2013.01) |

(52) U.S. Cl.
CPC ........... *B23K 26/20* (2013.01); *A61F 2220/005* (2013.01); *B23K 2203/14* (2013.01); *A61F 2/966* (2013.01); *B23K 2201/32* (2013.01); *A61F 2/856* (2013.01); *A61F 2/95* (2013.01); *A61F 2/954* (2013.01); *A61F 2002/9534* (2013.01); *A61F 2/962* (2013.01); *A61F 2/90* (2013.01); *A61F 2002/9517* (2013.01); *A61F 2002/9665* (2013.01); *D10B 2509/06* (2013.01)
USPC ........................................................ 623/1.12

(58) Field of Classification Search
CPC ............. A61F 2/95–2/958; A61F 2/962–2/97; A61F 2002/9505–2002/9665
USPC ........................ 606/108; 623/1.11, 1.12, 1.23
See application file for complete search history.

(56) References Cited

U.S. PATENT DOCUMENTS

| | | | |
|---|---|---|---|
| 2,836,181 | A | 5/1958 | Tapp |
| 2,936,257 | A | 5/1960 | Nailler et al. |

(Continued)

FOREIGN PATENT DOCUMENTS

| | | |
|---|---|---|
| CA | 2083157 | 11/1991 |
| CA | 2173664 | 10/1996 |

(Continued)

OTHER PUBLICATIONS

Murayama et al., "Nonadhesive liquid embolic agent for cerebral arteriovenous malformations: Preliminary histopathological studies in swine rete mirabile," Neurosurgery, 43:1164-1172, 1998.

(Continued)

*Primary Examiner* — Darwin Erezo
*Assistant Examiner* — Jonathan Hollm
(74) *Attorney, Agent, or Firm* — Jonathan D. Feuchtwang; Knobbe Martens Olson & Bear LLP

(57) ABSTRACT

Devices and methods for stent advancement, including methods for instructing another or others how to advance a stent into an anatomical structure or into a testing/demonstration synthetic structure, such as a polymer tube. The advancement may be achieved by at least two periods of stent engagement that drive a stent distally from a sheath separated by a period of non-engagement.

75 Claims, 21 Drawing Sheets

(56) References Cited

U.S. PATENT DOCUMENTS

| | | |
|---|---|---|
| 3,463,197 A | 8/1969 | Slade |
| 3,479,670 A | 11/1969 | Medell |
| 3,620,218 A | 11/1971 | Schmitt et al. |
| 3,868,956 A | 3/1975 | Alfidi et al. |
| 4,503,569 A | 3/1985 | Dotter |
| 4,580,568 A | 4/1986 | Gianturco |
| 4,619,246 A | 10/1986 | Molgaard-Nielsen et al. |
| 4,665,906 A | 5/1987 | Jervis |
| 4,733,665 A | 3/1988 | Palmaz |
| 4,739,762 A | 4/1988 | Palmaz |
| 4,768,507 A | 9/1988 | Fischell et al. |
| 4,771,773 A | 9/1988 | Kropf |
| 4,776,337 A | 10/1988 | Palmaz |
| 4,850,999 A | 7/1989 | Planck |
| 4,877,030 A | 10/1989 | Beck et al. |
| 4,922,905 A | 5/1990 | Strecker |
| 4,950,227 A | 8/1990 | Savin et al. |
| 4,954,126 A | 9/1990 | Wallsten |
| 4,960,410 A | 10/1990 | Pinchuk |
| 4,969,458 A | 11/1990 | Wiktor |
| 4,990,151 A | 2/1991 | Wallsten |
| 4,994,071 A | 2/1991 | MacGregor |
| 4,997,440 A | 3/1991 | Dumican |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,059,211 A | 10/1991 | Stack et al. |
| 5,064,435 A | 11/1991 | Porter |
| 5,067,957 A | 11/1991 | Jervis |
| 5,102,417 A | 4/1992 | Palmaz |
| 5,104,404 A | 4/1992 | Wolff |
| 5,107,852 A | 4/1992 | Davidson et al. |
| 5,116,365 A | 5/1992 | Hillstead |
| 5,133,732 A | 7/1992 | Wiktor |
| 5,135,536 A | 8/1992 | Hillstead |
| 5,159,920 A | 11/1992 | Condon et al. |
| 5,171,262 A | 12/1992 | MacGregor |
| 5,180,376 A | 1/1993 | Fischell |
| 5,190,546 A | 3/1993 | Jervis |
| 5,201,757 A | 4/1993 | Heyn et al. |
| 5,201,901 A | 4/1993 | Harada et al. |
| 5,211,658 A | 5/1993 | Clouse |
| 5,219,355 A | 6/1993 | Parodi et al. |
| 5,246,445 A | 9/1993 | Yachia et al. |
| 5,256,158 A | 10/1993 | Tolkoff et al. |
| 5,261,916 A | 11/1993 | Engelson |
| 5,282,823 A | 2/1994 | Schwartz et al. |
| 5,304,220 A | 4/1994 | Maginot |
| 5,306,286 A | 4/1994 | Stack et al. |
| 5,342,387 A | 8/1994 | Summers |
| 5,350,398 A | 9/1994 | Pavcnik et al. |
| 5,360,443 A | 11/1994 | Barone et al. |
| 5,366,504 A | 11/1994 | Andersen et al. |
| 5,372,600 A | 12/1994 | Beyar et al. .................. 623/1.11 |
| 5,376,077 A * | 12/1994 | Gomringer .............. 604/167.06 |
| 5,382,259 A | 1/1995 | Phelps et al. |
| 5,389,106 A | 2/1995 | Tower |
| 5,391,172 A | 2/1995 | Williams et al. |
| 5,395,390 A | 3/1995 | Simon et al. |
| 5,405,377 A | 4/1995 | Cragg |
| 5,405,378 A | 4/1995 | Strecker |
| 5,411,507 A | 5/1995 | Heckele |
| 5,411,549 A | 5/1995 | Peters |
| 5,415,664 A | 5/1995 | Pinchuk |
| 5,419,231 A | 5/1995 | Earle, III et al. |
| D359,802 S | 6/1995 | Fontaine |
| 5,425,739 A | 6/1995 | Jessen |
| 5,425,984 A | 6/1995 | Kennedy et al. |
| 5,433,723 A * | 7/1995 | Lindenberg et al. .......... 606/198 |
| 5,433,729 A | 7/1995 | Adams et al. ..................... 607/5 |
| 5,443,458 A | 8/1995 | Eury |
| 5,454,795 A | 10/1995 | Samson |
| 5,458,615 A | 10/1995 | Klemm et al. |
| 5,464,408 A | 11/1995 | Duc |
| 5,474,563 A | 12/1995 | Myler et al. |
| 5,476,508 A | 12/1995 | Amstrup |
| 5,478,355 A | 12/1995 | Muth et al. |
| 5,480,423 A | 1/1996 | Ravenscroft et al. |
| 5,484,425 A | 1/1996 | Fischell et al. |
| 5,484,444 A | 1/1996 | Braunschweiler et al. |
| 5,496,277 A | 3/1996 | Termin et al. .................. 604/104 |
| 5,507,769 A | 4/1996 | Marin et al. |
| 5,527,282 A | 6/1996 | Segal |
| 5,527,324 A | 6/1996 | Krantz et al. |
| 5,527,337 A | 6/1996 | Stack et al. |
| 5,534,007 A | 7/1996 | St. Germain et al. |
| 5,534,287 A | 7/1996 | Lukic |
| 5,536,274 A | 7/1996 | Neuss |
| 5,551,954 A | 9/1996 | Buscemi et al. |
| 5,554,181 A | 9/1996 | Das |
| 5,571,167 A | 11/1996 | Maginot |
| 5,571,168 A | 11/1996 | Toro |
| 5,573,520 A | 11/1996 | Schwartz et al. |
| 5,575,817 A | 11/1996 | Martin |
| 5,575,818 A | 11/1996 | Pinchuk ....................... 623/1.15 |
| 5,591,172 A | 1/1997 | Bachmann et al. |
| 5,591,195 A | 1/1997 | Taheri et al. |
| 5,591,199 A | 1/1997 | Porter et al. |
| 5,591,222 A | 1/1997 | Susawa et al. |
| 5,597,378 A | 1/1997 | Jervis |
| 5,603,698 A | 2/1997 | Roberts et al. |
| 5,607,445 A | 3/1997 | Summers |
| 5,607,466 A | 3/1997 | Imbert et al. |
| 5,609,627 A | 3/1997 | Goicoechea et al. |
| 5,628,754 A | 5/1997 | Shevlin et al. |
| 5,628,787 A | 5/1997 | Mayer |
| 5,629,077 A | 5/1997 | Turnland et al. |
| 5,630,840 A | 5/1997 | Mayer |
| 5,632,771 A | 5/1997 | Boatman et al. |
| 5,643,339 A | 7/1997 | Kavteladze et al. ......... 623/1.22 |
| 5,645,558 A | 7/1997 | Horton |
| 5,645,559 A | 7/1997 | Hachtman et al. |
| 5,653,684 A | 8/1997 | Laptewicz et al. |
| 5,653,727 A | 8/1997 | Wiktor |
| 5,662,703 A | 9/1997 | Yurek et al. |
| 5,662,713 A | 9/1997 | Andersen et al. |
| 5,667,523 A | 9/1997 | Bynon et al. |
| 5,669,880 A | 9/1997 | Solar |
| 5,669,924 A | 9/1997 | Shaknovich |
| 5,669,936 A | 9/1997 | Lazarus |
| 5,670,161 A | 9/1997 | Healy et al. |
| 5,674,276 A | 10/1997 | Andersen et al. |
| 5,674,277 A | 10/1997 | Freitag |
| 5,679,400 A | 10/1997 | Tuch |
| 5,679,470 A | 10/1997 | Mayer |
| 5,683,411 A | 11/1997 | Kavteladze et al. |
| 5,683,450 A | 11/1997 | Goicoechea et al. |
| 5,683,451 A | 11/1997 | Lenker et al. ................ 623/1.11 |
| 5,693,086 A | 12/1997 | Goicoechea et al. |
| 5,695,469 A | 12/1997 | Segal |
| 5,695,483 A | 12/1997 | Samson |
| 5,699,880 A | 12/1997 | Hockley |
| 5,700,269 A | 12/1997 | Pinchuk et al. |
| 5,702,373 A | 12/1997 | Samson |
| 5,702,418 A | 12/1997 | Ravenscroft |
| 5,707,376 A | 1/1998 | Kavteladze et al. ......... 623/1.11 |
| 5,709,701 A | 1/1998 | Parodi |
| 5,709,703 A | 1/1998 | Lukic et al. |
| 5,713,917 A | 2/1998 | Leonhardt et al. |
| 5,713,948 A * | 2/1998 | Uflacker ....................... 623/1.23 |
| 5,716,365 A | 2/1998 | Goicoechea et al. |
| 5,716,396 A | 2/1998 | Williams, Jr. |
| 5,718,159 A | 2/1998 | Thompson |
| 5,718,724 A | 2/1998 | Goicoechea et al. |
| 5,720,735 A | 2/1998 | Dorros |
| 5,725,571 A | 3/1998 | Imbert et al. |
| 5,725,572 A | 3/1998 | Lam et al. |
| 5,728,150 A | 3/1998 | McDonald et al. |
| 5,728,158 A | 3/1998 | Lau et al. |
| 5,733,267 A | 3/1998 | Del Toro |
| 5,733,327 A | 3/1998 | Igaki et al. |
| 5,741,325 A | 4/1998 | Chaikof et al. |
| 5,741,333 A | 4/1998 | Frid |

(56) References Cited

U.S. PATENT DOCUMENTS

| | | | | |
|---|---|---|---|---|
| 5,749,880 A | | 5/1998 | Banas et al. | |
| 5,749,921 A | * | 5/1998 | Lenker et al. | 623/1.42 |
| 5,755,708 A | | 5/1998 | Segal | |
| 5,758,562 A | | 6/1998 | Thompson | |
| 5,759,186 A | | 6/1998 | Bachmann et al. | |
| 5,766,204 A | | 6/1998 | Porter et al. | |
| 5,766,219 A | | 6/1998 | Horton | |
| 5,766,237 A | | 6/1998 | Cragg | |
| 5,766,710 A | | 6/1998 | Turnlund et al. | |
| 5,769,882 A | | 6/1998 | Fogarty et al. | |
| 5,772,668 A | | 6/1998 | Summers et al. | 623/1.11 |
| 5,776,142 A | | 7/1998 | Gunderson | 623/1.11 |
| 5,776,180 A | | 7/1998 | Goicoechea et al. | |
| 5,792,156 A | | 8/1998 | Perouse | |
| 5,797,952 A | | 8/1998 | Klein | |
| 5,800,508 A | | 9/1998 | Goicoechea et al. | |
| 5,800,511 A | | 9/1998 | Mayer | |
| 5,807,398 A | | 9/1998 | Shaknovich | |
| 5,824,041 A | | 10/1998 | Lenker et al. | |
| 5,824,053 A | | 10/1998 | Khosravi et al. | |
| 5,824,058 A | | 10/1998 | Ravenscroft et al. | |
| 5,824,077 A | | 10/1998 | Mayer | |
| 5,830,229 A | | 11/1998 | Konya et al. | |
| 5,836,966 A | | 11/1998 | St. Germain | |
| RE35,988 E | | 12/1998 | Winston et al. | |
| 5,843,168 A | | 12/1998 | Dang | |
| 5,849,037 A | | 12/1998 | Frid | |
| 5,851,217 A | | 12/1998 | Wolff et al. | |
| 5,860,998 A | | 1/1999 | Robinson et al. | |
| 5,876,386 A | | 3/1999 | Samson | |
| 5,876,432 A | | 3/1999 | Lau et al. | |
| 5,888,201 A | | 3/1999 | Stinson et al. | |
| 5,891,191 A | | 4/1999 | Stinson | |
| 5,902,332 A | | 5/1999 | Schatz | |
| 5,911,731 A | | 6/1999 | Pham et al. | |
| 5,913,896 A | | 6/1999 | Boyle et al. | |
| 5,916,196 A | | 6/1999 | Andrea et al. | |
| 5,916,263 A | | 6/1999 | Goicoechea et al. | |
| 5,928,279 A | | 7/1999 | Shannon et al. | |
| 5,928,280 A | | 7/1999 | Hansen et al. | |
| 5,931,842 A | | 8/1999 | Goldsteen et al. | |
| 5,938,696 A | | 8/1999 | Goicoechea et al. | |
| 5,941,908 A | | 8/1999 | Goldsteen et al. | |
| 5,944,738 A | | 8/1999 | Amplatz et al. | |
| 5,954,729 A | | 9/1999 | Bachmann et al. | |
| 5,954,764 A | | 9/1999 | Parodi | |
| 5,964,771 A | | 10/1999 | Beyar et al. | |
| 5,968,052 A | | 10/1999 | Sullivan, III et al. | 623/1.11 |
| 5,968,088 A | | 10/1999 | Hansen et al. | |
| 5,972,017 A | | 10/1999 | Berg et al. | |
| 5,976,155 A | | 11/1999 | Foreman et al. | |
| 5,976,178 A | | 11/1999 | Goldsteen et al. | |
| 5,989,276 A | | 11/1999 | Houser et al. | |
| 6,004,348 A | | 12/1999 | Banas et al. | |
| 6,007,574 A | | 12/1999 | Pulnev et al. | |
| 6,015,424 A | | 1/2000 | Rosenbluth et al. | |
| 6,017,319 A | | 1/2000 | Jacobsen et al. | |
| 6,019,778 A | | 2/2000 | Wilson et al. | |
| 6,019,785 A | | 2/2000 | Strecker | |
| 6,019,786 A | | 2/2000 | Thompson | |
| 6,024,763 A | | 2/2000 | Lenker et al. | |
| 6,027,529 A | | 2/2000 | Roychowdhury et al. | |
| 6,036,702 A | | 3/2000 | Bachinski et al. | |
| 6,039,755 A | | 3/2000 | Edwin et al. | |
| 6,042,588 A | | 3/2000 | Munsinger et al. | |
| 6,042,589 A | | 3/2000 | Marianne | |
| 6,042,605 A | | 3/2000 | Martin et al. | |
| 6,048,338 A | | 4/2000 | Larson et al. | |
| 6,051,020 A | | 4/2000 | Goicoechea et al. | |
| 6,053,943 A | | 4/2000 | Edwin et al. | |
| 6,059,752 A | | 5/2000 | Segal | |
| 6,063,113 A | | 5/2000 | Kavteladze et al. | |
| 6,077,295 A | | 6/2000 | Limon et al. | |
| 6,080,191 A | | 6/2000 | Summers | |
| 6,090,115 A | | 7/2000 | Beyar et al. | |
| 6,090,125 A | | 7/2000 | Horton | |
| 6,102,890 A | | 8/2000 | Stivland et al. | |
| 6,102,932 A | | 8/2000 | Kurz | |
| 6,117,167 A | | 9/2000 | Goicoechea et al. | |
| 6,120,432 A | | 9/2000 | Sullivan et al. | |
| 6,120,522 A | | 9/2000 | Vrba et al. | |
| 6,123,115 A | | 9/2000 | Greenhalgh | |
| 6,123,723 A | | 9/2000 | Kónya et al. | |
| 6,124,523 A | | 9/2000 | Banas et al. | |
| 6,126,685 A | | 10/2000 | Lenker et al. | |
| 6,136,007 A | | 10/2000 | Goldsteen et al. | |
| 6,146,415 A | | 11/2000 | Fitz | |
| 6,149,681 A | | 11/2000 | Houser et al. | |
| 6,152,945 A | | 11/2000 | Bachinski et al. | |
| 6,156,062 A | | 12/2000 | McGuinness | |
| 6,159,239 A | | 12/2000 | Greenhalgh | |
| 6,164,339 A | | 12/2000 | Greenhalgh | |
| 6,165,213 A | | 12/2000 | Goicoechea et al. | |
| 6,168,622 B1 | | 1/2001 | Mazzocchi | |
| 6,171,326 B1 | | 1/2001 | Ferrera et al. | |
| 6,172,617 B1 | | 1/2001 | Bullock | |
| 6,183,508 B1 | | 2/2001 | Stinson et al. | |
| 6,186,942 B1 | | 2/2001 | Sullivan et al. | |
| 6,192,944 B1 | | 2/2001 | Greenhalgh | |
| 6,206,912 B1 | | 3/2001 | Goldsteen et al. | |
| 6,237,460 B1 | | 5/2001 | Frid | |
| 6,238,402 B1 | | 5/2001 | Sullivan, III et al. | |
| 6,238,430 B1 | | 5/2001 | Klumb et al. | |
| 6,241,757 B1 | | 6/2001 | An et al. | |
| 6,245,103 B1 | | 6/2001 | Stinson | |
| 6,248,112 B1 | | 6/2001 | Gambale et al. | |
| 6,248,122 B1 | | 6/2001 | Klumb et al. | |
| 6,251,132 B1 | | 6/2001 | Ravenscroft et al. | |
| 6,258,080 B1 | | 7/2001 | Samson | |
| 6,261,315 B1 | | 7/2001 | St. Germain et al. | |
| 6,264,684 B1 | | 7/2001 | Banas et al. | |
| 6,264,689 B1 | | 7/2001 | Colgan et al. | |
| 6,270,521 B1 | | 8/2001 | Fischell et al. | |
| 6,280,467 B1 | | 8/2001 | Leonhardt | |
| 6,293,955 B1 | | 9/2001 | Houser et al. | |
| 6,293,965 B1 | | 9/2001 | Berg et al. | |
| 6,295,714 B1 | | 10/2001 | Roychowdhury et al. | |
| 6,296,622 B1 | | 10/2001 | Kurz et al. | |
| 6,302,893 B1 | | 10/2001 | Limon et al. | |
| 6,302,905 B1 | | 10/2001 | Goldsteen et al. | |
| 6,302,906 B1 | | 10/2001 | Goicoechea et al. | |
| 6,306,105 B1 | | 10/2001 | Rooney et al. | |
| 6,306,141 B1 | | 10/2001 | Jervis | |
| 6,309,415 B1 | | 10/2001 | Pulnev et al. | |
| 6,312,454 B1 | | 11/2001 | Stockel et al. | |
| 6,319,267 B1 | | 11/2001 | Kurz | |
| 6,325,822 B1 | | 12/2001 | Chouinard et al. | |
| 6,331,184 B1 | | 12/2001 | Abrams | |
| 6,336,938 B1 | | 1/2002 | Kavteladze et al. | 623/1.15 |
| 6,342,068 B1 | | 1/2002 | Thompson | |
| 6,346,118 B1 | * | 2/2002 | Baker et al. | 623/1.12 |
| 6,348,048 B1 | | 2/2002 | Andrea et al. | |
| 6,350,278 B1 | | 2/2002 | Lenker et al. | |
| 6,352,531 B1 | | 3/2002 | O'Connor et al. | |
| 6,355,060 B1 | | 3/2002 | Lenker et al. | |
| 6,361,637 B2 | | 3/2002 | Martin et al. | |
| 6,371,953 B1 | | 4/2002 | Beyar et al. | |
| 6,371,979 B1 | | 4/2002 | Beyar et al. | |
| 6,379,365 B1 | | 4/2002 | Diaz | |
| 6,383,214 B1 | | 5/2002 | Banas et al. | |
| 6,383,216 B1 | | 5/2002 | Kavteladze et al. | |
| 6,391,051 B2 | | 5/2002 | Sullivan, III et al. | |
| 6,398,802 B1 | | 6/2002 | Yee | |
| 6,398,803 B1 | | 6/2002 | Layne et al. | |
| 6,409,750 B1 | | 6/2002 | Hyodoh et al. | |
| 6,419,694 B1 | | 7/2002 | Sandock | |
| 6,423,085 B1 | | 7/2002 | Murayama et al. | |
| 6,425,898 B1 | | 7/2002 | Wilson et al. | |
| 6,440,161 B1 | | 8/2002 | Madrid et al. | |
| 6,447,522 B2 | | 9/2002 | Gambale et al. | |
| 6,451,025 B1 | | 9/2002 | Jervis | |
| 6,451,033 B1 | | 9/2002 | Berg et al. | |
| 6,451,047 B2 | | 9/2002 | McCrea et al. | |
| 6,451,052 B1 | | 9/2002 | Burmeister et al. | |

(56) References Cited

U.S. PATENT DOCUMENTS

| | | |
|---|---|---|
| 6,468,301 B1 | 10/2002 | Amplatz et al. |
| 6,475,184 B1 | 11/2002 | Wang et al. |
| 6,475,209 B1 | 11/2002 | Larson et al. |
| 6,488,700 B2 | 12/2002 | Klumb et al. |
| 6,506,204 B2 | 1/2003 | Mazzocchi |
| 6,514,196 B1 | 2/2003 | Sullivan et al. |
| 6,514,261 B1 | 2/2003 | Randall et al. ............ 606/108 |
| 6,520,983 B1 | 2/2003 | Colgan et al. |
| 6,520,986 B2 | 2/2003 | Martin et al. |
| 6,527,802 B1 | 3/2003 | Mayer |
| 6,533,805 B1 | 3/2003 | Jervis |
| 6,554,798 B1 | 4/2003 | Mann et al. |
| 6,558,414 B2 | 5/2003 | Layne |
| 6,559,312 B2 | 5/2003 | Krauss et al. |
| 6,562,064 B1 | 5/2003 | deBeer |
| 6,572,645 B2 | 6/2003 | Leonhardt |
| 6,576,006 B2 | 6/2003 | Limon et al. |
| 6,579,314 B1 | 6/2003 | Lombardi et al. |
| 6,582,461 B1 | 6/2003 | Burmeister et al. |
| 6,585,695 B1 | 7/2003 | Adair et al. |
| 6,592,617 B2 | 7/2003 | Thompson |
| 6,599,296 B1 | 7/2003 | Gillick et al. ............ 606/108 |
| 6,605,102 B1 | 8/2003 | Mazzocchi et al. |
| 6,607,551 B1 | 8/2003 | Sullivan et al. |
| 6,613,075 B1 | 9/2003 | Healy et al. |
| 6,629,981 B2 | 10/2003 | Bui et al. |
| 6,638,291 B1 | 10/2003 | Ferrera et al. |
| 6,641,608 B1 | 11/2003 | Pulnev et al. |
| 6,645,237 B2 | 11/2003 | Klumb et al. |
| 6,652,544 B2 | 11/2003 | Houser et al. |
| 6,656,212 B2 | 12/2003 | Ravenscroft et al. |
| 6,660,030 B2 | 12/2003 | Shaolian et al. |
| 6,673,883 B1 | 1/2004 | Rowan |
| 6,679,903 B2 | 1/2004 | Kurz |
| 6,689,162 B1 | 2/2004 | Thompson |
| 6,695,862 B2 | 2/2004 | Cox et al. |
| 6,699,273 B2 | 3/2004 | Langan |
| 6,702,829 B2 | 3/2004 | Bachinski et al. |
| 6,709,379 B1 | 3/2004 | Brandau et al. |
| 6,712,835 B2 | 3/2004 | Mazzocchi et al. |
| 6,719,934 B2 | 4/2004 | Stinson |
| 6,726,712 B1 | 4/2004 | Raeder-Devens et al. |
| 6,730,117 B1 | 5/2004 | Tseng et al. |
| 6,733,519 B2 | 5/2004 | Lashinski et al. |
| 6,736,839 B2 | 5/2004 | Cummings |
| 6,736,840 B2 | 5/2004 | Fischell et al. |
| 6,740,077 B1 | 5/2004 | Brandau et al. |
| 6,740,115 B2 | 5/2004 | Lombardi et al. |
| 6,743,219 B1 | 6/2004 | Dwyer et al. |
| 6,749,627 B2 | 6/2004 | Thompson et al. |
| 6,755,854 B2 | 6/2004 | Gillick et al. |
| 6,758,858 B2 | 7/2004 | McCrea et al. |
| 6,770,087 B2 | 8/2004 | Layne et al. |
| 6,773,446 B1 | 8/2004 | Dwyer et al. |
| 6,776,791 B1 | 8/2004 | Stallings et al. |
| 6,790,226 B2 | 9/2004 | Edwin et al. |
| 6,792,979 B2 | 9/2004 | Konya et al. ............ 140/92.1 |
| 6,797,217 B2 | 9/2004 | McCrea et al. |
| RE38,653 E | 11/2004 | Igaki et al. |
| 6,814,750 B2 | 11/2004 | Kavteladze et al. |
| 6,846,316 B2 | 1/2005 | Abrams |
| RE38,711 E | 3/2005 | Igaki et al. |
| 6,859,986 B2 | 3/2005 | Jackson et al. |
| 6,860,898 B2 | 3/2005 | Stack et al. |
| 6,866,669 B2 | 3/2005 | Buzzard et al. ............ 606/108 |
| 6,866,679 B2 | 3/2005 | Kusleika |
| 6,913,618 B2 | 7/2005 | Denardo et al. |
| 6,926,732 B2 | 8/2005 | Derus et al. ............ 623/1.12 |
| 6,932,837 B2 | 8/2005 | Amplatz et al. |
| 6,939,352 B2 | 9/2005 | Buzzard et al. ............ 606/108 |
| 6,942,654 B1 | 9/2005 | Schaefer et al. |
| 6,942,688 B2 | 9/2005 | Bartholf et al. |
| 6,949,103 B2 | 9/2005 | Mazzocchi et al. |
| 6,962,597 B2 | 11/2005 | Goodin |
| 6,974,472 B2 | 12/2005 | Hong et al. ............ 623/1.15 |
| 6,989,019 B2 | 1/2006 | Mazzocchi et al. |
| 6,989,024 B2 | 1/2006 | Hebert et al. |
| 6,997,948 B2 | 2/2006 | Stinson |
| 7,001,420 B2 | 2/2006 | Speck et al. |
| 7,018,401 B1 | 3/2006 | Hyodoh et al. ............ 623/1.12 |
| 7,022,133 B2 | 4/2006 | Yee et al. |
| 7,033,375 B2 | 4/2006 | Mazzocchi et al. |
| 7,037,330 B1 | 5/2006 | Rivelli, Jr. et al. |
| 7,048,014 B2 | 5/2006 | Hyodoh et al. ............ 140/92.1 |
| 7,048,752 B2 | 5/2006 | Mazzocchi et al. |
| 7,052,511 B2 | 5/2006 | Weldon et al. ............ 623/1.11 |
| 7,052,513 B2 | 5/2006 | Thompson |
| 7,060,150 B2 | 6/2006 | Banas et al. |
| 7,070,607 B2 | 7/2006 | Murayama et al. |
| 7,083,631 B2 | 8/2006 | Houser et al. |
| 7,083,640 B2 | 8/2006 | Lombardi et al. |
| 7,094,248 B2 | 8/2006 | Bachinski et al. |
| 7,105,016 B2 | 9/2006 | Shiu et al. ............ 623/1.12 |
| 7,115,141 B2 | 10/2006 | Menz et al. |
| 7,122,050 B2 | 10/2006 | Randall et al. ............ 623/1.23 |
| 7,137,993 B2 | 11/2006 | Acosta et al. |
| 7,147,618 B2 | 12/2006 | Kurz |
| 7,147,655 B2 | 12/2006 | Chermoni |
| 7,156,860 B2 | 1/2007 | Wallsten |
| 7,160,323 B2 | 1/2007 | Pulnev et al. |
| 7,172,617 B2 | 2/2007 | Colgan et al. |
| 7,175,650 B2 | 2/2007 | Ruetsch |
| 7,211,095 B2 | 5/2007 | Bachinski et al. |
| 7,211,109 B2 | 5/2007 | Thompson |
| 7,241,308 B2 | 7/2007 | Andreas et al. |
| 7,270,668 B2 | 9/2007 | Andreas et al. |
| 7,279,005 B2 | 10/2007 | Stinson |
| 7,306,756 B2 | 12/2007 | Edwin et al. |
| 7,309,349 B2 | 12/2007 | Jackson et al. |
| 7,314,481 B2 | 1/2008 | Karpiel |
| 7,316,701 B2 | 1/2008 | Ferrera et al. |
| 7,316,708 B2 | 1/2008 | Gordon et al. |
| 7,320,702 B2 | 1/2008 | Hammersmark et al. |
| 7,326,236 B2 | 2/2008 | Andreas et al. |
| 7,329,279 B2 | 2/2008 | Haug et al. |
| 7,344,514 B2 | 3/2008 | Shanley |
| 7,344,558 B2 | 3/2008 | Lorenzo et al. |
| 7,367,985 B2 | 5/2008 | Mazzocchi et al. |
| 7,367,986 B2 | 5/2008 | Mazzocchi et al. |
| 7,367,987 B2 | 5/2008 | Balgobin et al. |
| 7,371,250 B2 | 5/2008 | Mazzocchi et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,381,219 B2 | 6/2008 | Salahieh et al. |
| 7,387,640 B2 | 6/2008 | Cummings |
| 7,396,362 B2 | 7/2008 | Jervis |
| 7,402,170 B2 | 7/2008 | McCullagh et al. ......... 623/1.16 |
| 7,404,820 B2 | 7/2008 | Mazzocchi et al. |
| 7,410,492 B2 | 8/2008 | Mazzocchi et al. |
| 7,419,502 B2 | 9/2008 | Pulnev et al. |
| 7,419,503 B2 | 9/2008 | Pulnev et al. |
| 7,442,200 B2 | 10/2008 | Mazzocchi et al. |
| 7,445,631 B2 | 11/2008 | Salahieh et al. |
| 7,462,192 B2 | 12/2008 | Norton et al. |
| 7,468,071 B2 | 12/2008 | Edwin et al. |
| 7,491,224 B2 | 2/2009 | Cox et al. |
| 7,500,989 B2 | 3/2009 | Solem et al. |
| 7,510,570 B1 | 3/2009 | Goicoechea et al. |
| 7,517,361 B1 | 4/2009 | Ravenscroft |
| 7,520,893 B2 | 4/2009 | Rivelli, Jr. |
| 7,527,632 B2 | 5/2009 | Houghton et al. |
| 7,527,643 B2 | 5/2009 | Case et al. |
| 7,534,250 B2 | 5/2009 | Schaeffer et al. |
| RE40,816 E | 6/2009 | Taylor et al. |
| 7,550,001 B2 | 6/2009 | Dorn et al. |
| 7,550,002 B2 | 6/2009 | Goto et al. |
| 7,553,322 B2 | 6/2009 | Dorn et al. |
| 7,553,323 B1 | 6/2009 | Perez et al. |
| 7,556,635 B2 | 7/2009 | Mazzocchi et al. |
| 7,556,636 B2 | 7/2009 | Mazzocchi et al. |
| 7,566,338 B2 | 7/2009 | Mazzocchi et al. |
| 7,566,342 B2 | 7/2009 | Parker et al. |
| 7,572,273 B2 | 8/2009 | Mazzocchi et al. |

(56) References Cited

U.S. PATENT DOCUMENTS

| | | | |
|---|---|---|---|
| 7,578,829 B2 | 8/2009 | Goldsteen et al. | |
| 7,578,830 B2 | 8/2009 | Kusleika et al. | |
| 7,578,838 B2 | 8/2009 | Melsheimer | |
| 7,578,899 B2 | 8/2009 | Edwin et al. | |
| 7,582,101 B2 | 9/2009 | Jones et al. | |
| 7,604,661 B2 | 10/2009 | Pavcnik et al. | |
| 7,608,058 B2 | 10/2009 | Wilson et al. | |
| 7,608,099 B2 | 10/2009 | Johnson et al. | |
| 7,611,528 B2 | 11/2009 | Goodson, IV et al. | |
| 7,621,946 B2 | 11/2009 | Turner et al. | |
| 7,628,803 B2 | 12/2009 | Pavcnik et al. | |
| 7,637,934 B2 | 12/2009 | Mangiardi et al. | |
| 7,655,039 B2 | 2/2010 | Leanna et al. | |
| 7,666,218 B2 | 2/2010 | Klein et al. | |
| 7,670,355 B2 | 3/2010 | Mazzocchi et al. | |
| 7,670,356 B2 | 3/2010 | Mazzocchi et al. | |
| 7,678,130 B2 | 3/2010 | Mazzocchi et al. | |
| 7,686,815 B2 | 3/2010 | Mazzocchi et al. | |
| 7,691,124 B2 | 4/2010 | Balgobin | |
| 7,695,507 B2 | 4/2010 | Rivelli, Jr. et al. | |
| 7,717,923 B2 | 5/2010 | Kennedy, II et al. | |
| 7,717,949 B2 | 5/2010 | Dorn | |
| 7,736,386 B2 | 6/2010 | Pulnev et al. | |
| 7,748,389 B2 | 7/2010 | Salahieh et al. | |
| 7,763,068 B2 | 7/2010 | Pulnev et al. | |
| 7,780,720 B2 | 8/2010 | Goicoechea et al. | |
| 7,785,340 B2 | 8/2010 | Heidner et al. | |
| 7,794,489 B2 | 9/2010 | Shumer et al. | |
| 7,806,919 B2 | 10/2010 | Bloom et al. | |
| 2001/0010007 A1 | 7/2001 | Bachinski et al. | |
| 2001/0025131 A1 | 9/2001 | Edwin et al. | |
| 2001/0032010 A1 | 10/2001 | Sandock | |
| 2001/0049547 A1 | 12/2001 | Moore | |
| 2001/0051809 A1 | 12/2001 | Houser et al. | |
| 2002/0019659 A1 | 2/2002 | Goicoechea et al. | |
| 2002/0022857 A1 | 2/2002 | Goldsteen et al. | |
| 2002/0087046 A1 | 7/2002 | Sullivan et al. | |
| 2002/0087181 A1 | 7/2002 | Goldsteen et al. | |
| 2002/0138095 A1 | 9/2002 | Mazzocchi et al. | |
| 2002/0151955 A1* | 10/2002 | Tran et al. | 623/1.12 |
| 2002/0169474 A1 | 11/2002 | Kusleika et al. | |
| 2002/0173810 A1 | 11/2002 | Bachinski et al. | |
| 2003/0009215 A1 | 1/2003 | Mayer | |
| 2003/0014062 A1 | 1/2003 | Houser et al. | |
| 2003/0014063 A1 | 1/2003 | Houser et al. | |
| 2003/0040771 A1* | 2/2003 | Hyodoh et al. | 606/200 |
| 2003/0040772 A1 | 2/2003 | Hyodoh et al. | 606/200 |
| 2003/0050686 A1 | 3/2003 | Raeder-Devens et al. | |
| 2003/0083541 A1 | 5/2003 | Sullivan et al. | |
| 2003/0109886 A1 | 6/2003 | Keegan et al. | |
| 2003/0130721 A1 | 7/2003 | Martin et al. | |
| 2003/0208263 A1 | 11/2003 | Burmeister et al. | |
| 2003/0216803 A1 | 11/2003 | Ledergerber | |
| 2004/0073287 A1 | 4/2004 | Goicoechea et al. | |
| 2004/0093056 A1 | 5/2004 | Johnson et al. | |
| 2004/0098081 A1* | 5/2004 | Landreville et al. | 623/1.11 |
| 2004/0098115 A1 | 5/2004 | Goicoechea et al. | |
| 2004/0106979 A1 | 6/2004 | Goicoechea et al. | |
| 2004/0117004 A1 | 6/2004 | Osborne et al. | |
| 2004/0133264 A1 | 7/2004 | Moore | |
| 2004/0167599 A1 | 8/2004 | Goicoechea et al. | |
| 2004/0181239 A1 | 9/2004 | Dorn et al. | 606/108 |
| 2004/0193179 A1 | 9/2004 | Nikolchev | |
| 2004/0199240 A1 | 10/2004 | Dorn | |
| 2004/0230286 A1 | 11/2004 | Moore et al. | |
| 2004/0236402 A1 | 11/2004 | Layne et al. | |
| 2004/0267348 A1* | 12/2004 | Gunderson et al. | 623/1.12 |
| 2005/0021123 A1 | 1/2005 | Dorn et al. | 623/1.11 |
| 2005/0059889 A1 | 3/2005 | Mayer | |
| 2005/0065590 A1 | 3/2005 | Shelso | |
| 2005/0080475 A1 | 4/2005 | Andreas et al. | |
| 2005/0085892 A1 | 4/2005 | Goto et al. | |
| 2005/0090893 A1 | 4/2005 | Kavteladze et al. | |
| 2005/0113902 A1 | 5/2005 | Geiser et al. | |
| 2005/0119690 A1 | 6/2005 | Mazzocchi et al. | |
| 2005/0137686 A1 | 6/2005 | Salahieh et al. | |
| 2005/0137687 A1 | 6/2005 | Salahieh et al. | |
| 2005/0137688 A1 | 6/2005 | Salahieh et al. | |
| 2005/0137689 A1 | 6/2005 | Salahieh et al. | |
| 2005/0137691 A1 | 6/2005 | Salahieh et al. | |
| 2005/0137692 A1 | 6/2005 | Haug et al. | |
| 2005/0137694 A1 | 6/2005 | Haug et al. | |
| 2005/0137695 A1 | 6/2005 | Salahieh et al. | |
| 2005/0137696 A1 | 6/2005 | Salahieh et al. | |
| 2005/0137697 A1 | 6/2005 | Salahieh et al. | |
| 2005/0137699 A1 | 6/2005 | Salahieh et al. | |
| 2005/0137701 A1 | 6/2005 | Salahieh et al. | |
| 2005/0143809 A1 | 6/2005 | Salahieh et al. | |
| 2005/0149160 A1 | 7/2005 | McFerran | |
| 2005/0154439 A1 | 7/2005 | Gunderson | |
| 2005/0182475 A1 | 8/2005 | Jen et al. | |
| 2005/0209670 A1 | 9/2005 | George et al. | 623/1.11 |
| 2005/0209671 A1 | 9/2005 | Ton et al. | 623/1.11 |
| 2005/0209672 A1 | 9/2005 | George et al. | 623/1.11 |
| 2005/0209675 A1 | 9/2005 | Ton et al. | 623/1.11 |
| 2005/0209676 A1 | 9/2005 | Kusleika | |
| 2005/0216051 A1 | 9/2005 | Mazzocchi et al. | |
| 2005/0246010 A1 | 11/2005 | Alexander et al. | 623/1.12 |
| 2005/0288764 A1 | 12/2005 | Snow et al. | |
| 2006/0015168 A1 | 1/2006 | Gunderson | |
| 2006/0036309 A1 | 2/2006 | Hebert et al. | |
| 2006/0058835 A1 | 3/2006 | Murayama et al. | |
| 2006/0058865 A1 | 3/2006 | Case | |
| 2006/0058872 A1 | 3/2006 | Salahieh et al. | |
| 2006/0074478 A1 | 4/2006 | Feller, III | |
| 2006/0100687 A1 | 5/2006 | Fahey et al. | |
| 2006/0116750 A1 | 6/2006 | Hebert et al. | |
| 2006/0136034 A1 | 6/2006 | Modesitt et al. | |
| 2006/0161195 A1 | 7/2006 | Goldsteen et al. | |
| 2006/0173524 A1 | 8/2006 | Salahieh et al. | |
| 2006/0184224 A1 | 8/2006 | Angel | |
| 2006/0184226 A1 | 8/2006 | Austin | |
| 2006/0212105 A1 | 9/2006 | Dorn et al. | |
| 2006/0229714 A1 | 10/2006 | Lombardi et al. | |
| 2006/0241686 A1 | 10/2006 | Ferrera et al. | |
| 2006/0253191 A1 | 11/2006 | Salahieh et al. | |
| 2006/0276873 A1 | 12/2006 | Sato | |
| 2007/0010876 A1 | 1/2007 | Salahieh et al. | |
| 2007/0010877 A1 | 1/2007 | Salahieh et al. | |
| 2007/0021821 A1 | 1/2007 | Johnson et al. | |
| 2007/0043420 A1 | 2/2007 | Lostetter | |
| 2007/0083253 A1 | 4/2007 | Fischell et al. | |
| 2007/0093889 A1 | 4/2007 | Wu et al. | |
| 2007/0100421 A1 | 5/2007 | Griffin | |
| 2007/0106367 A1 | 5/2007 | Ruetsch | |
| 2007/0118206 A1 | 5/2007 | Colgan et al. | |
| 2007/0118207 A1 | 5/2007 | Amplatz et al. | |
| 2007/0118214 A1 | 5/2007 | Salahieh et al. | |
| 2007/0156223 A1* | 7/2007 | Vaughan | 623/1.11 |
| 2007/0162103 A1 | 7/2007 | Case et al. | |
| 2007/0162107 A1 | 7/2007 | Haug et al. | |
| 2007/0173868 A1 | 7/2007 | Bachinski et al. | |
| 2007/0198076 A1 | 8/2007 | Hebert et al. | |
| 2007/0203503 A1 | 8/2007 | Salahieh et al. | |
| 2007/0203563 A1 | 8/2007 | Hebert et al. | |
| 2007/0208405 A1 | 9/2007 | Goodin et al. | |
| 2007/0219612 A1 | 9/2007 | Andreas et al. | |
| 2007/0219616 A1 | 9/2007 | Modesitt et al. | |
| 2007/0219617 A1 | 9/2007 | Saint | |
| 2007/0233224 A1 | 10/2007 | Leynov et al. | |
| 2007/0244540 A1 | 10/2007 | Pryor | |
| 2007/0244552 A1 | 10/2007 | Salahieh et al. | |
| 2007/0250151 A1 | 10/2007 | Pereira | |
| 2007/0255386 A1 | 11/2007 | Tenne | |
| 2007/0265697 A1 | 11/2007 | Goicoechea et al. | |
| 2007/0270930 A1 | 11/2007 | Schenck | |
| 2007/0270932 A1 | 11/2007 | Headley et al. | |
| 2007/0270936 A1 | 11/2007 | Andreas et al. | |
| 2007/0282420 A1 | 12/2007 | Gunderson | |
| 2007/0293928 A1 | 12/2007 | Tomlin | |
| 2007/0293929 A1 | 12/2007 | Aoba et al. | |
| 2007/0299500 A1 | 12/2007 | Hebert et al. | |
| 2007/0299501 A1 | 12/2007 | Hebert et al. | |
| 2007/0299502 A1 | 12/2007 | Hebert et al. | |

(56) References Cited

U.S. PATENT DOCUMENTS

| | | | |
|---|---|---|---|
| 2008/0004685 | A1 | 1/2008 | Seemann et al. |
| 2008/0039863 | A1 | 2/2008 | Keegan et al. |
| 2008/0065147 | A1 | 3/2008 | Mazzocchi et al. |
| 2008/0071308 | A1 | 3/2008 | Mazzocchi et al. |
| 2008/0091257 | A1 | 4/2008 | Andreas et al. |
| 2008/0097572 | A1 | 4/2008 | Sheldon et al. |
| 2008/0109059 | A1 | 5/2008 | Gordon et al. |
| 2008/0125806 | A1 | 5/2008 | Mazzocchi et al. |
| 2008/0125849 | A1 | 5/2008 | Burpee et al. |
| 2008/0125859 | A1 | 5/2008 | Salahieh et al. |
| 2008/0132989 | A1 | 6/2008 | Snow et al. |
| 2008/0183272 | A1 | 7/2008 | Wood et al. |
| 2008/0221654 | A1 | 9/2008 | Buiser et al. |
| 2008/0234795 | A1 | 9/2008 | Snow et al. |
| 2008/0234796 | A1 | 9/2008 | Dorn |
| 2008/0234814 | A1 | 9/2008 | Salahieh et al. |
| 2008/0262591 | A1 | 10/2008 | Shin et al. |
| 2008/0288043 | A1 | 11/2008 | Kaufmann et al. |
| 2008/0290076 | A1 | 11/2008 | Sheldon et al. |
| 2008/0294231 | A1 | 11/2008 | Aguilar et al. |
| 2008/0300667 | A1 | 12/2008 | Hebert et al. |
| 2009/0030495 | A1 | 1/2009 | Koch |
| 2009/0036967 | A1 | 2/2009 | Cummings |
| 2009/0054969 | A1 | 2/2009 | Salahieh et al. |
| 2009/0082841 | A1 | 3/2009 | Zacharias et al. |
| 2009/0099637 | A1 | 4/2009 | Barthold et al. |
| 2009/0099643 | A1 | 4/2009 | Hyodeh et al. |
| 2009/0125092 | A1 | 5/2009 | McCrea et al. |
| 2009/0143849 | A1 | 6/2009 | Ozawa et al. |
| 2009/0149936 | A1 | 6/2009 | Lentz |
| 2009/0157162 | A1 | 6/2009 | Chow et al. |
| 2009/0171427 | A1 | 7/2009 | Melsheimer et al. |
| 2009/0177260 | A1 | 7/2009 | Aggerholm |
| 2009/0177264 | A1 | 7/2009 | Ravenscroft |
| 2009/0182407 | A1 | 7/2009 | Leanna et al. |
| 2009/0182410 | A1 | 7/2009 | Case et al. |
| 2009/0228092 | A1 | 9/2009 | Raeder-Devens et al. |
| 2009/0234428 | A1 | 9/2009 | Snow et al. |
| 2009/0234443 | A1 | 9/2009 | Ottma et al. |
| 2009/0254168 | A1 | 10/2009 | Parker et al. |
| 2009/0276028 | A1 | 11/2009 | Bailey et al. |
| 2009/0276030 | A1 | 11/2009 | Kusleika |
| 2009/0276033 | A1 | 11/2009 | Mayer |
| 2009/0299449 | A1 | 12/2009 | Styrc |
| 2009/0299451 | A1 | 12/2009 | Ellsworth et al. |
| 2009/0299461 | A1 | 12/2009 | Chermoni |
| 2009/0311132 | A1 | 12/2009 | Banas et al. |
| 2009/0312829 | A1 | 12/2009 | Aoba et al. |
| 2010/0004729 | A1 | 1/2010 | Chew et al. |
| 2010/0004732 | A1 | 1/2010 | Johnson et al. |
| 2010/0010617 | A1 | 1/2010 | Goodson, IV et al. |
| 2010/0030320 | A1 | 2/2010 | Feller, IIII |
| 2010/0042198 | A1 | 2/2010 | Burton |
| 2010/0042199 | A1 | 2/2010 | Burton |
| 2010/0057191 | A1 | 3/2010 | Pavcnik et al. |
| 2010/0094399 | A1 | 4/2010 | Dorn et al. |
| 2010/0204774 | A1 | 8/2010 | Goodin et al. |
| 2010/0286756 | A1 | 11/2010 | Dorn et al. |
| 2011/0295354 | A1 | 12/2011 | Bueche et al. |

FOREIGN PATENT DOCUMENTS

| | | |
|---|---|---|
| CA | 2247891 | 9/1997 |
| CA | 2272947 | 6/1998 |
| DE | 3618734 | 12/1986 |
| DE | 3902364 | 8/1989 |
| DE | 4104702 | 8/1992 |
| DE | 4235004 | 4/1993 |
| DE | 4420142 | 12/1995 |
| DE | 68927998 | 9/1997 |
| DE | 19703482 | 8/1998 |
| DE | 29919625 | 1/2000 |
| DE | 69131423 | 1/2000 |
| DE | 19910188 | 5/2000 |
| DE | 102005020785 | 11/2006 |
| DE | 102006053748 | 4/2008 |
| DE | 202010007592 | 10/2010 |
| EP | 0145166 | 6/1985 |
| EP | 0518839 | 12/1992 |
| EP | 0528039 | 2/1993 |
| EP | 0686379 | 12/1995 |
| EP | 0689807 | 1/1996 |
| EP | 0696447 | 2/1996 |
| EP | 0701800 | 3/1996 |
| EP | 0722700 | 7/1996 |
| EP | 0737452 | 10/1996 |
| EP | 0740928 | 11/1996 |
| EP | 0743047 | 11/1996 |
| EP | 0744163 | 11/1996 |
| EP | 0744164 | 11/1996 |
| EP | 0747021 | 12/1996 |
| EP | 0782841 | 7/1997 |
| EP | 0788012 | 8/1997 |
| EP | 0788802 | 8/1997 |
| EP | 0792627 | 9/1997 |
| EP | 0804909 | 11/1997 |
| EP | 0804934 | 11/1997 |
| EP | 0812579 | 12/1997 |
| EP | 0857471 | 8/1998 |
| EP | 0893108 | 1/1999 |
| EP | 0894505 | 2/1999 |
| EP | 0941716 | 9/1999 |
| EP | 0943302 | 9/1999 |
| EP | 0948946 | 10/1999 |
| EP | 1010406 | 6/2000 |
| EP | 1025813 | 8/2000 |
| EP | 1121911 | 8/2001 |
| EP | 1208816 | 5/2002 |
| EP | 1221307 | 7/2002 |
| EP | 1275352 | 1/2003 |
| EP | 1396239 | 3/2004 |
| EP | 1402847 | 3/2004 |
| EP | 1447058 | 8/2004 |
| EP | 1520557 | 4/2005 |
| EP | 1582178 | 10/2005 |
| EP | 1637092 | 3/2006 |
| EP | 1803423 | 7/2007 |
| EP | 1834610 | 9/2007 |
| EP | 1844739 | 10/2007 |
| EP | 1872742 | 1/2008 |
| EP | 1900382 | 3/2008 |
| EP | 1941845 | 7/2008 |
| FR | 2678508 | 1/1993 |
| FR | 2735967 | 1/1997 |
| GB | 1183497 | 3/1970 |
| GB | 1205743 | 9/1970 |
| GB | 1565828 | 4/1980 |
| GB | 2135585 | 9/1984 |
| JP | 59-500652 | 4/1984 |
| JP | 07-508199 | 9/1995 |
| JP | 09-506540 | 6/1997 |
| JP | 09-173469 | 7/1997 |
| JP | 09-511160 | 11/1997 |
| JP | 09-512460 | 12/1997 |
| JP | 10-043313 | 2/1998 |
| JP | 10-272190 | 10/1998 |
| JP | 11-057021 | 3/1999 |
| JP | 11-57021 | 3/1999 |
| JP | 2004-510490 | 4/2004 |
| JP | 2005-342539 | 12/2005 |
| JP | 2006-522649 | 5/2006 |
| RU | 2454205 | 6/2012 |
| SU | 1457921 | 2/1989 |
| WO | WO 83/03752 | 11/1983 |
| WO | WO 87/04935 | 8/1987 |
| WO | WO 89/03197 | 4/1989 |
| WO | WO 90/05554 | 5/1990 |
| WO | WO 91/17789 | 11/1991 |
| WO | WO 92/14408 | 9/1992 |
| WO | WO 94/00178 | 1/1994 |
| WO | WO 94/00179 | 1/1994 |
| WO | WO 94/03127 | 2/1994 |
| WO | WO 94/16646 | 8/1994 |

(56) References Cited

FOREIGN PATENT DOCUMENTS

| WO | WO 94/22379 | 10/1994 |
|---|---|---|
| WO | WO 94/27667 | 12/1994 |
| WO | WO 95/17859 | 7/1995 |
| WO | WO 95/21592 | 8/1995 |
| WO | WO 95/27448 | 10/1995 |
| WO | WO 95/29646 | 11/1995 |
| WO | WO 95/31945 | 11/1995 |
| WO | WO 96/01591 | 1/1996 |
| WO | WO 96/17645 | 6/1996 |
| WO | WO 96/19953 | 7/1996 |
| WO | WO 96/28115 | 9/1996 |
| WO | WO 96/31174 | 10/1996 |
| WO | WO96/31174 | 10/1996 |
| WO | WO 96/32078 | 10/1996 |
| WO | WO 96/33677 | 10/1996 |
| WO | WO 96/40000 | 12/1996 |
| WO | WO 96/41589 | 12/1996 |
| WO | WO 97/09932 | 3/1997 |
| WO | WO 97/16133 | 5/1997 |
| WO | WO 97/21401 | 6/1997 |
| WO | WO 97/21403 | 6/1997 |
| WO | WO 97/26939 | 7/1997 |
| WO | WO 97/32546 | 9/1997 |
| WO | WO 97/48343 | 12/1997 |
| WO | WO 98/11847 | 3/1998 |
| WO | WO 98/19625 | 5/1998 |
| WO | WO 98/19629 | 5/1998 |
| WO | WO 98/19630 | 5/1998 |
| WO | WO 98/19636 | 5/1998 |
| WO | WO 98/23241 | 6/1998 |
| WO | WO 98/29043 | 7/1998 |
| WO | WO 98/33453 | 8/1998 |
| WO | WO 98/33454 | 8/1998 |
| WO | WO 98/46168 | 10/1998 |
| WO | WO 98/55027 | 12/1998 |
| WO | WO 99/04728 | 2/1999 |
| WO | WO 99/32051 | 7/1999 |
| WO | WO 99/43379 | 9/1999 |
| WO | WO 99/44538 | 9/1999 |
| WO | WO 00/09059 | 2/2000 |
| WO | WO 00/12016 | 3/2000 |
| WO | WO 00/18330 | 4/2000 |
| WO | WO 00/25841 | 5/2000 |
| WO | WO 00/44306 | 8/2000 |
| WO | WO 00/45741 | 8/2000 |
| WO | WO 00/45742 | 8/2000 |
| WO | WO 00/45743 | 8/2000 |
| WO | WO 00/48660 | 8/2000 |
| WO | WO 00/49973 | 8/2000 |
| WO | WO 00/71059 | 11/2000 |
| WO | WO 01/72240 | 10/2001 |
| WO | WO 02/066091 | 8/2002 |
| WO | WO 02/087470 | 11/2002 |
| WO | WO 02/102279 | 12/2002 |
| WO | WO 03/003944 | 1/2003 |
| WO | WO 03/073963 | 9/2003 |
| WO | WO 2004/016201 | 2/2004 |
| WO | WO 2004/080504 | 9/2004 |
| WO | WO 2004/091441 | 10/2004 |
| WO | WO 2005-062980 | 7/2005 |
| WO | WO 2006/088638 | 8/2006 |
| WO | WO 2008/027902 | 3/2008 |
| WO | WO 2008/051941 | 5/2008 |
| WO | WO 2008/063496 | 5/2008 |

OTHER PUBLICATIONS

Punekar et al., "Post-surgical recurrent varicocele: efficacy of internal spermatic venography and steel-coil embolization," Br. J. Urol., 77:124:128, 1996.
White et al., "Pulmonary Arteriovenous Malformations: Techniques and Long-term Outcome of Embolotherapy," Radiology, 169:663-669, 1988.
JVIR Supplement, Scientific Program, SCVIR 22$^{nd}$ Annual Scientific Meeting, Mar. 8-13, 1997, Sheraton Washington Hotel, 8(1) Part 2, pp. 251-252, Jan.-Feb. 1997.
International Preliminary Report on Patentability and Written Opinion of the International Searching Authority for International Application No. PCT/US2007/082165, mailed on Apr. 22, 2009, in 25 pages.
Notification Concerning Transmittal of International Preliminary Report on Patentability, issued in International Application No. PCT/US2007/082148, mailed Apr. 30, 2009.
International Search Report and Written Opinion, issued in International Application No. PCT/US2007/082165, dated Apr. 2, 2008.
International Search Report and Written Opinion of the International Searching Authority for International Application No. PCT/US07/082148, mailed on Mar. 6, 2008.
Office Action issued in German Patent Application No. 202010007592.0 on Mar. 31, 2011.
Office Action issued in Israel Patent Application No. 198303 on Feb. 23, 2011.
Notification on the Grant for Patent Right for Invention issued in Chinese Patent Application No. 200780046619.4 on Nov. 29, 2011.
Office Action issued in Mexican Patent Application No. MX/a/2009/004292 on Oct. 26, 2011.
Office Action issued in Russian Patent Application No. 2009119252 on Oct. 6, 2011.
Office Action issued in Japanese Patent Application No. 2009-534804 on May 23, 2012.
Search Report and Written Opinion mailed Dec. 19, 2011 in International application No. PCT/US2011/038456.
Decision of Rejection issued in Japanese Patent Application No. 2009-534804 on Mar. 26, 2013.
Notice of Acceptance issued in Australian Patent Application No. 2007309087 on Jun. 19, 2012.
Notice of Allowance issued in Mexican Patent Application No. MX/a/2009/004292 on Feb. 12, 2013.
Notice of Reasons of Rejection issued in Japanese Patent Application No. 2012-209331 on Aug. 9, 2013.
Office Action in European Application No. 07844525.1 dated Sep. 13, 2013 in 5 pages.
Office Action issued in Australian Patent Application No. 2012202653 on May 3, 2013.
Office Action issued in Canadian Patent Application No. 2667322 on May 27, 2013.
Office Action issued in Chinese Patent Application No. 200780046619.4 on Jun. 24, 2011.
Office Action issued in Mexican Patent Application No. MX/a/2009/004292 on Jul. 3, 2012.

* cited by examiner

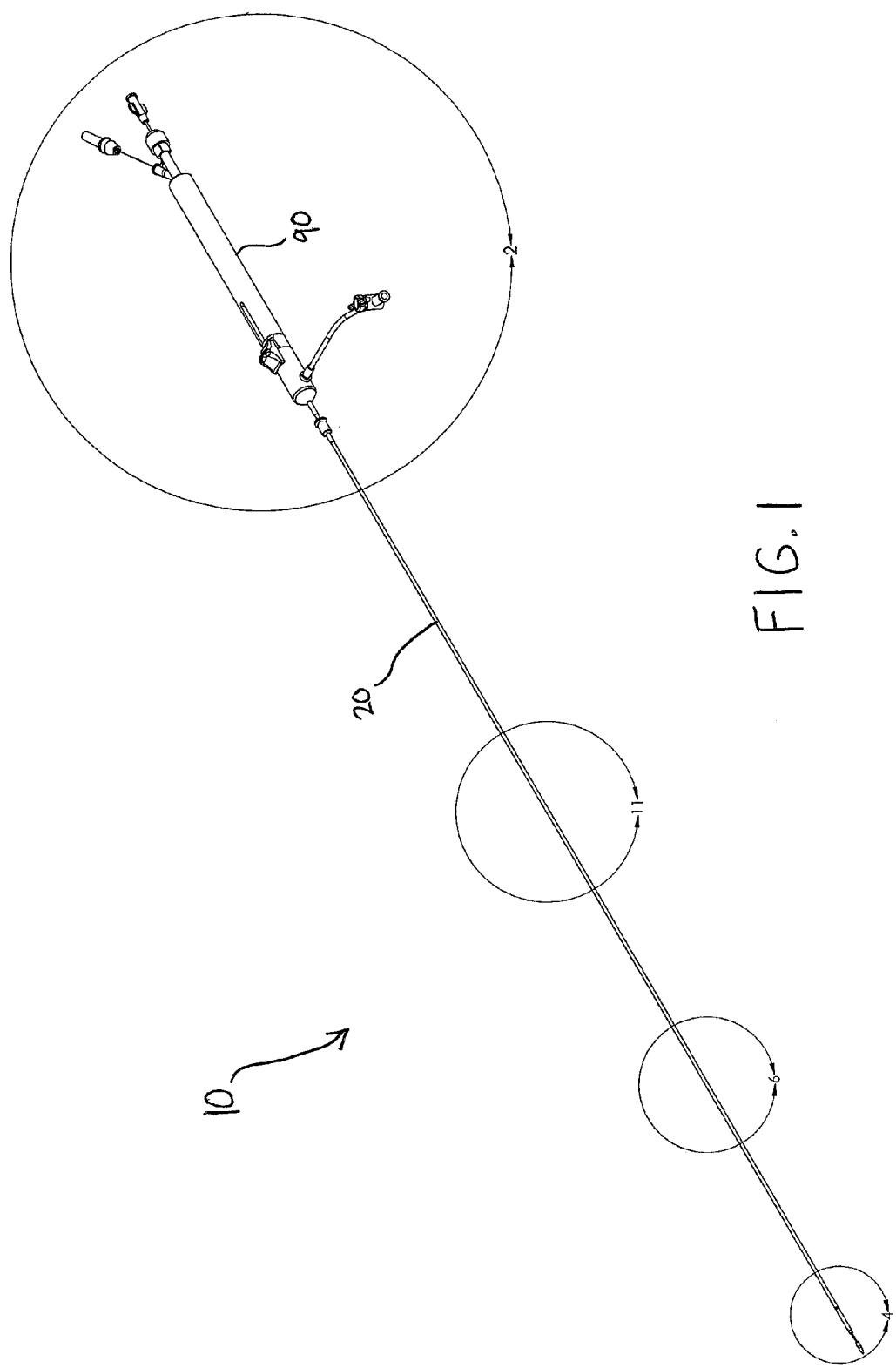

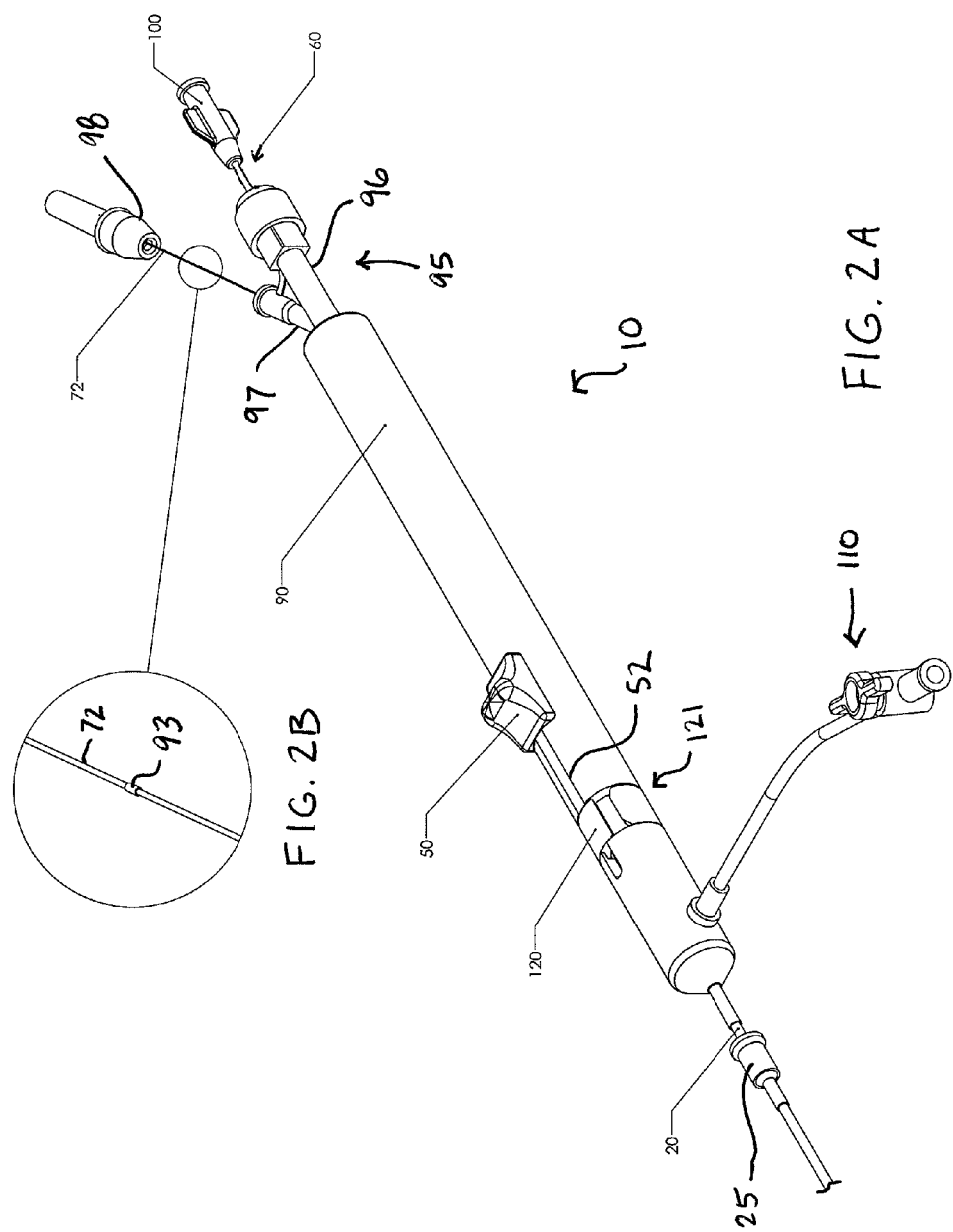

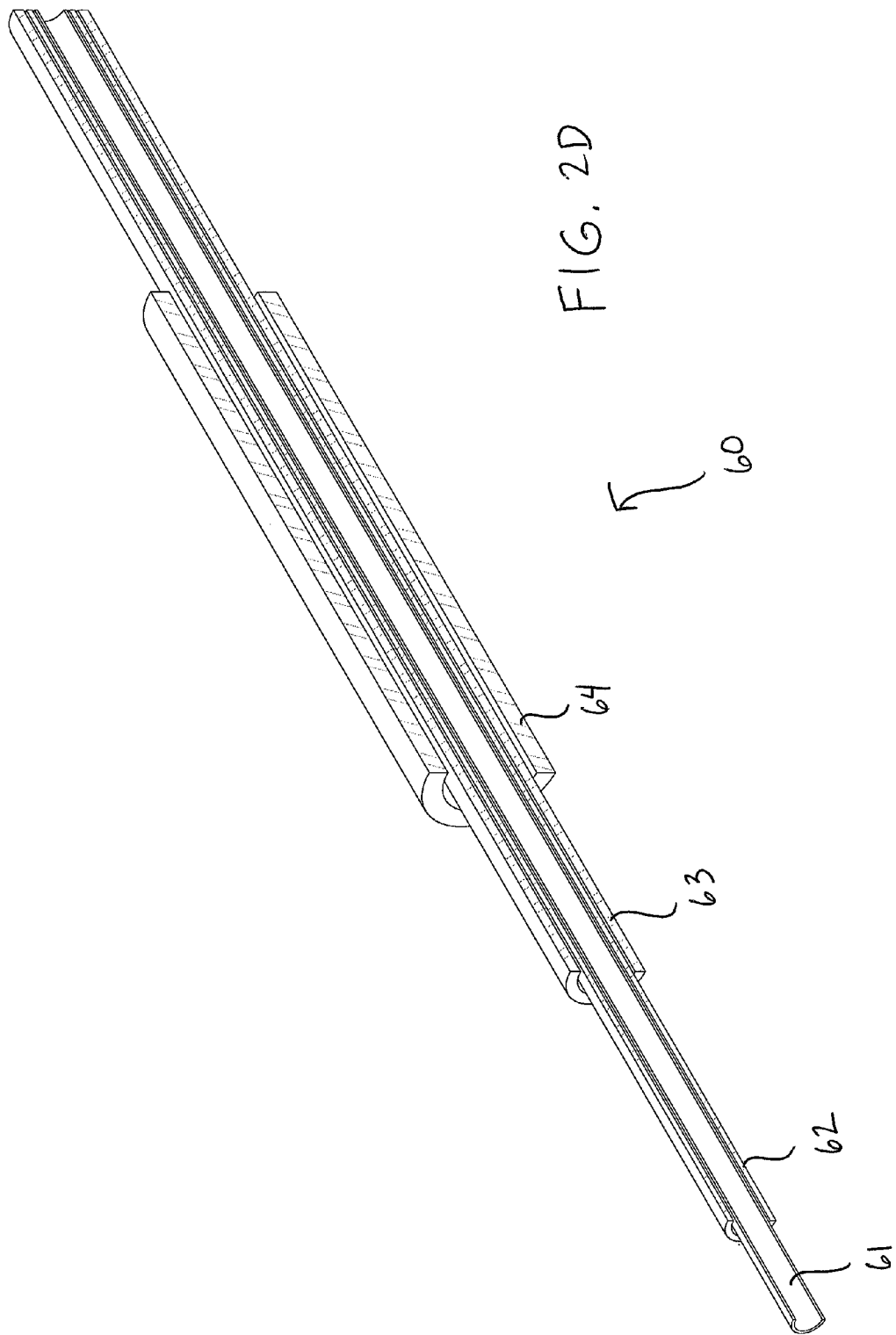

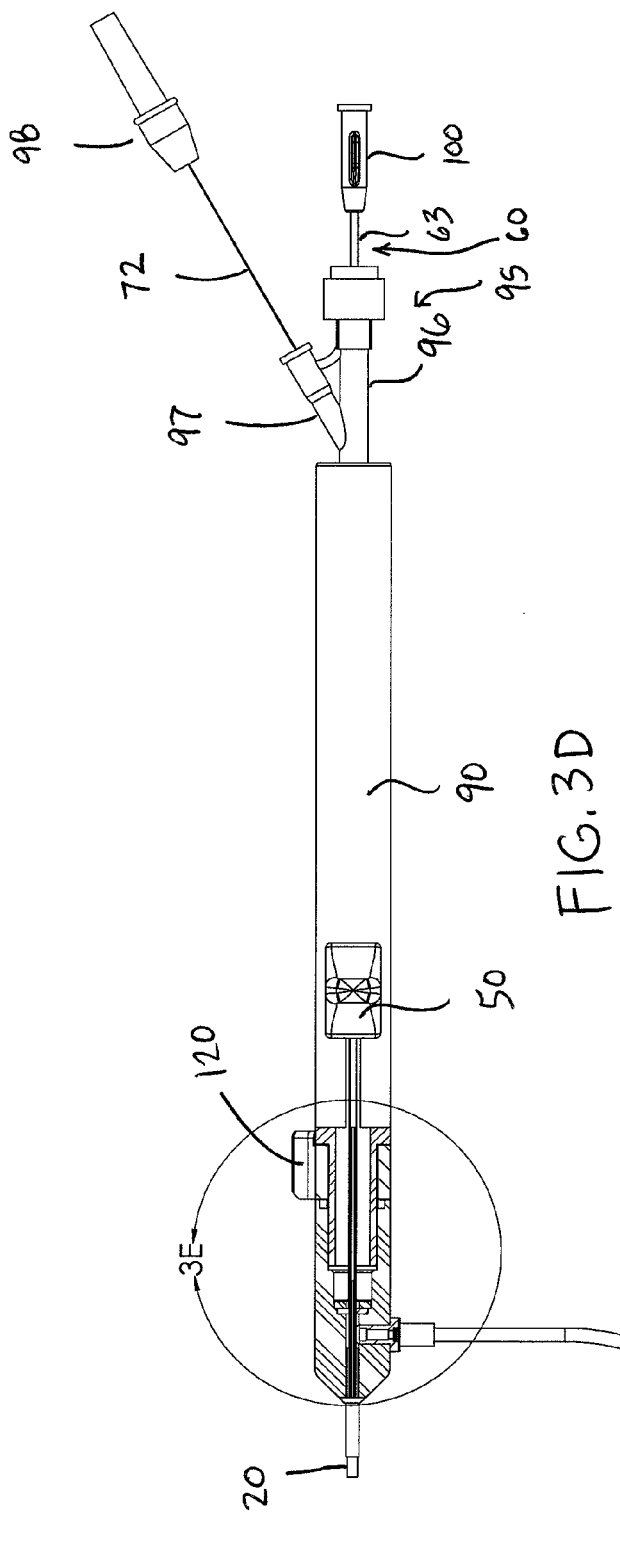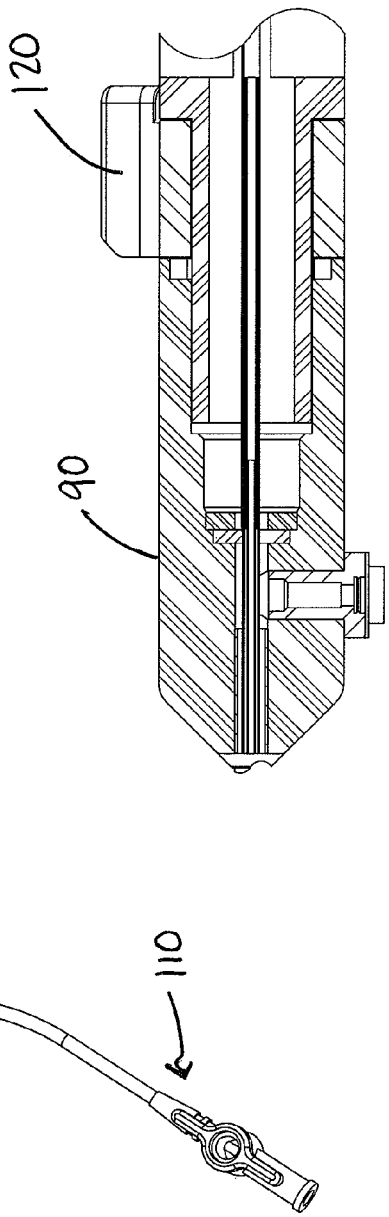
FIG. 3D
FIG. 3E

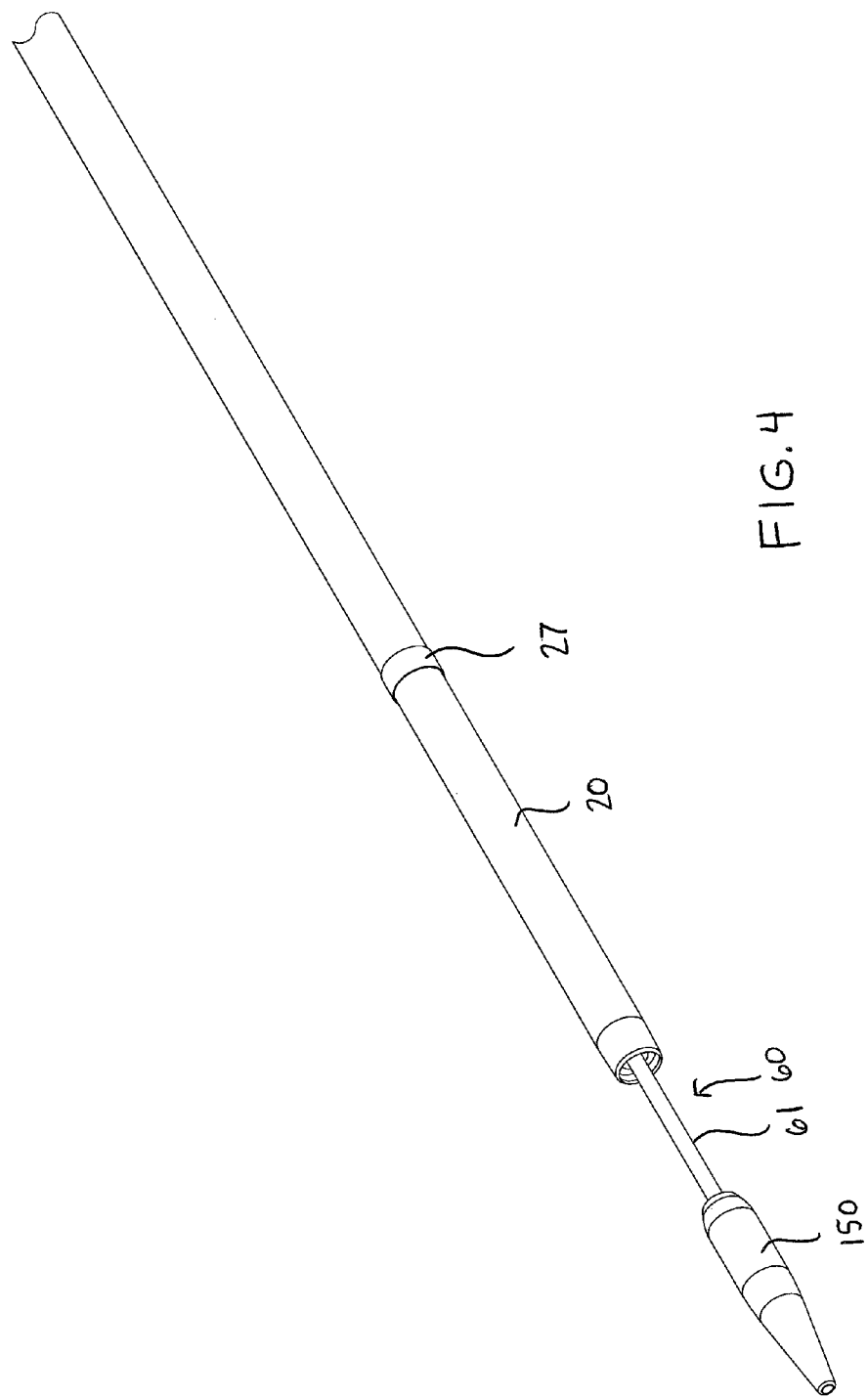

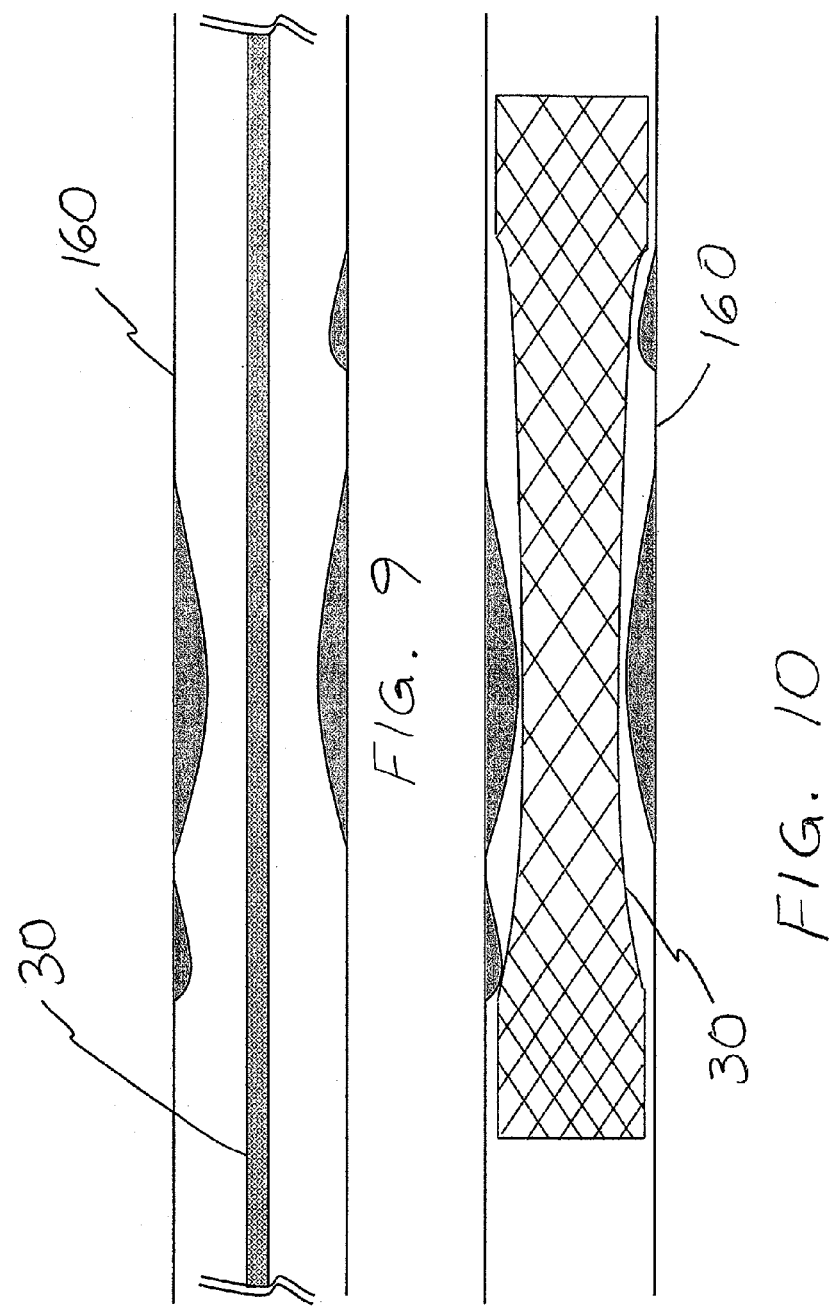

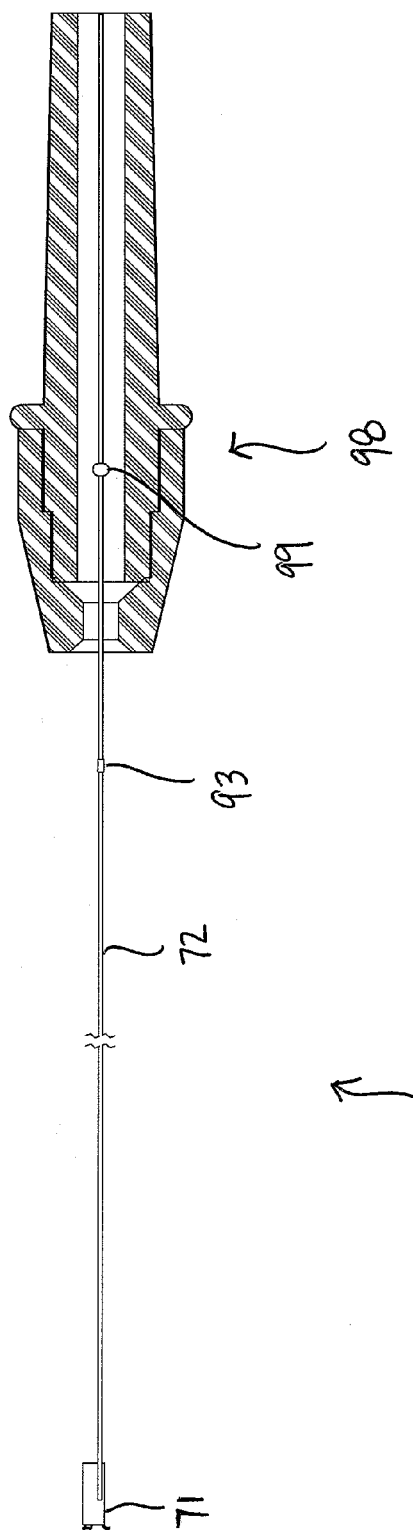

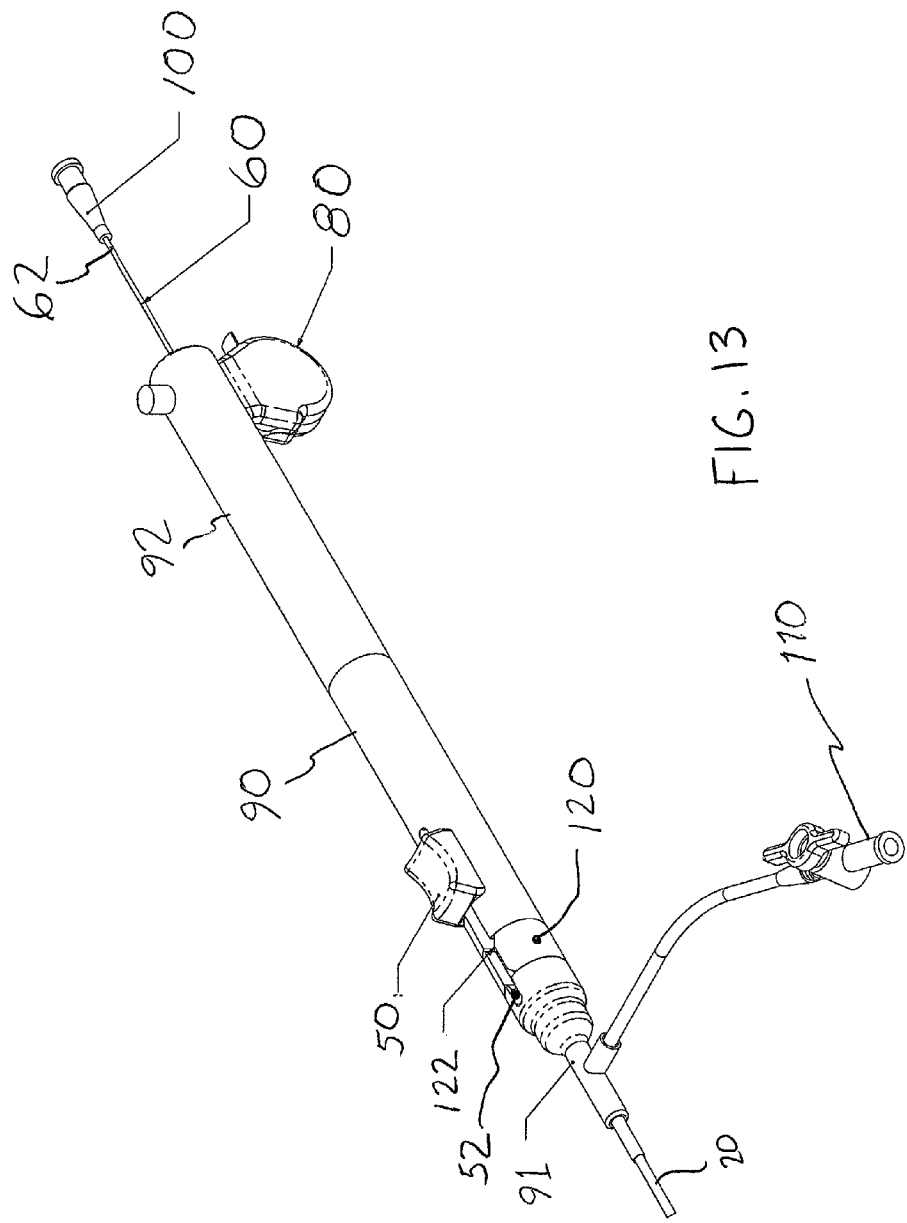

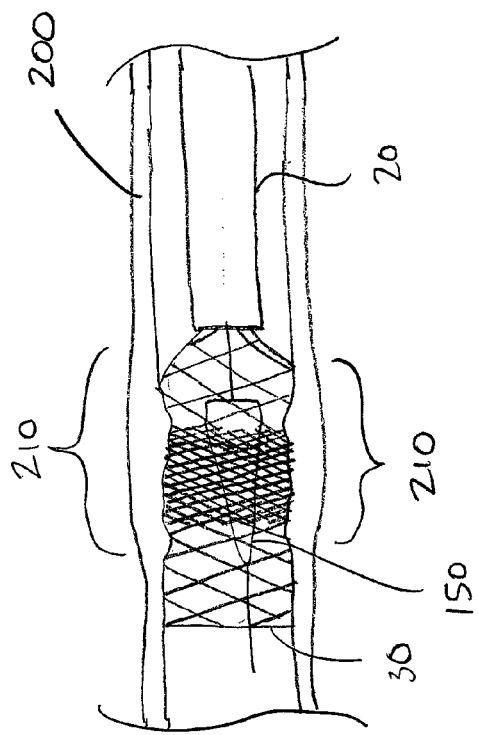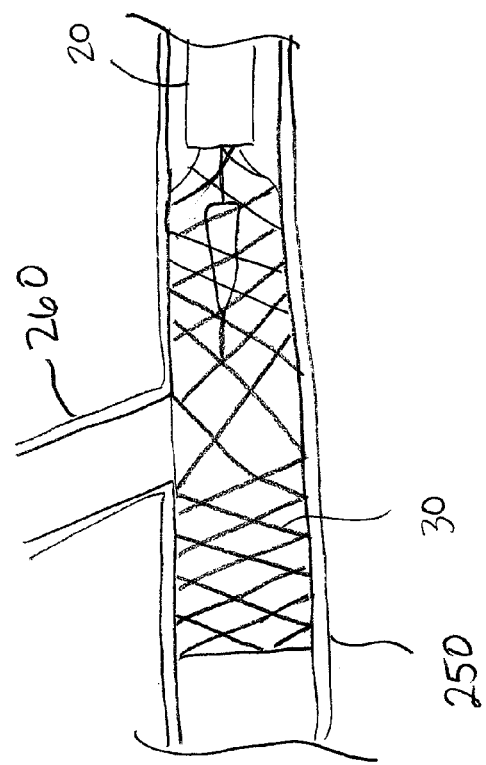

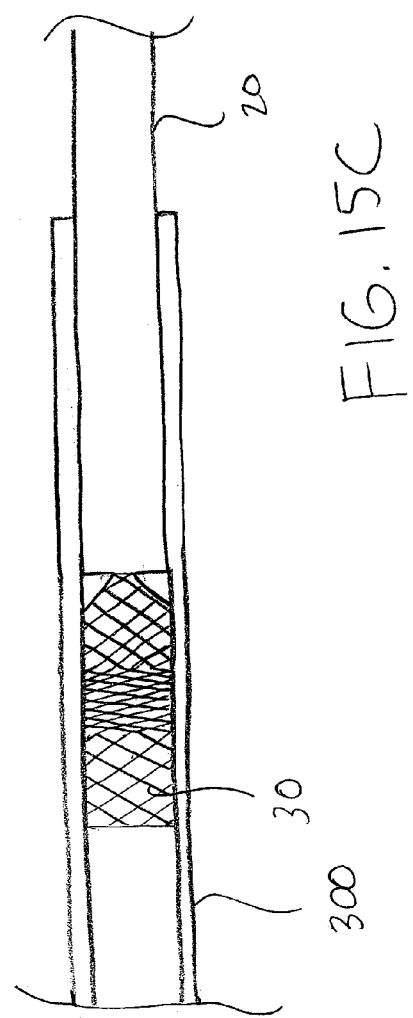

DEVICES FOR STENT ADVANCEMENT

CROSS-REFERENCE(S) TO RELATED APPLICATION(S)

This application claims priority to U.S. Provisional Patent Application Ser. No. 60/862,456, filed Oct. 22, 2006, the entire contents of which are expressly incorporated by reference.

BACKGROUND

1. Field

The present invention relates generally to devices and methods for stent placement, such as in a body vessel or duct or in a structure used for testing or demonstration (such as a polymer tube), and to methods of instructing one or more individuals on stent placement.

2. Description of Related Art

Examples of stent delivery devices are included in U.S. Pat. Nos. 5,372,600; 5,433,723; 5,707,376; 5,772,668; 5,776,142; 5,968,052; 6,514,261; 6,599,296; 7,052,511; 7,122,050; U.S. Pat. App. Pub. No. 20030040772; and U.S. Pat. App. Pub. No. 20050021123.

SUMMARY OF THE INVENTION

Some embodiments of the present devices (which also may be characterized as stent deployment devices) include an outer sheath; a stent disposed within the outer sheath, the stent having a distal end and a proximal end; a stent-engaging element positioned at least partially within the lumen of the stent; and a stent-retention element coupled to the proximal end of the stent; where the device is configured such that: the stent-engaging element can be operated in a reciprocating manner to engage and advance the stent distally at least partially out of the outer sheath; and the stent-retention element will stay in contact with the stent during proximal movement of the stent-engaging element provided that the proximal end of the stent is disposed within the outer sheath.

Some embodiments of the present devices include an outer sheath; a stent disposed within the outer sheath, the stent having a lumen, a distal end and a proximal end; an inner element positioned at least partially within the lumen of the stent, the inner element being configured to accept a guidewire; and a stent-engaging element positioned at least partially within the lumen of the stent and being capable of moving distally and proximally while the inner element is stationary; where the device is configured to distally drive the stent at least partially out of the outer sheath through at least two periods of engagement of the stent by the stent-engaging element that are separated by a period of non-engagement that does not drive the stent distally.

Some embodiments of the present devices include an outer sheath; a handle coupled to the outer sheath such that the outer sheath cannot move relative to the handle, the handle having a proximal end; a stent disposed within the outer sheath, the stent having a lumen, a distal end and a proximal end; and a stent-engaging element positioned at least partially within the lumen of the stent; where the device is configured such that: a user can advance the stent distally out of the outer sheath through at least two periods of engagement of the stent by the stent-engaging element that drive the stent distally and that are separated by a period of non-engagement that does not drive the stent distally; and the user's proximal-most point of contact with the device that causes each period of engagement is located at or distal of the proximal end of the handle.

Some embodiments of the present devices include an outer sheath; a stent disposed within the outer sheath, the stent having a distal end and a proximal end; a reciprocating element disposed at least partially within the outer sheath, the reciprocating element having a stent-engaging portion (which also may be characterized as a stent-engaging element); a user-actuatable element coupled to the reciprocating element; and a stent-retention element coupled to the proximal end of the stent; wherein: the stent-engaging portion is operable in a reciprocating manner to engage and advance the stent distally at least partially out of the outer sheath; and the stent-retention element stays in contact with the stent during proximal movement of the stent-engaging portion provided that the proximal end of the stent is disposed within the outer sheath.

Some embodiments of the present devices include an outer sheath; a stent disposed within the outer sheath, the stent having a distal end and a proximal end; a device body coupled to the outer sheath; a reciprocating element disposed at least partially within the outer sheath, the reciprocating element having a stent-engaging portion; and a user-actuatable element mounted on the device body and coupled to the reciprocating element; wherein the device is configured such that the stent-engaging portion is operable in a reciprocating manner to engage and advance the stent at least partially out of the outer sheath, and the outer sheath need not move relative to the device body in order for the stent-engaging portion to advance the stent.

Some embodiments of the present devices include an outer sheath; a stent disposed within the outer sheath, the stent having a distal end and a proximal end; a device body coupled to the outer sheath; a hollow reciprocating element disposed at least partially within the outer sheath, the hollow reciprocating element having a stent-engaging portion; a user-actuatable element mounted on the device body and coupled to the hollow reciprocating element; a stent-retention element coupled to the proximal end of the stent; and an inner tube disposed at least partially within the outer sheath, a portion of the inner tube being at least partially within the hollow reciprocating element; wherein: the hollow reciprocating element is operable to move (a) distally in response to a user moving the user-actuatable element distally and (b) proximally in response to a user moving the user-actuable element proximally; the stent-engaging portion is operable in a reciprocating manner to engage and advance the stent at least partially out of the outer sheath; the outer sheath need not move relative to the device body in order for the stent-engaging portion to advance the stent; the stent-retention element stays in contact with the stent during proximal movement of the stent-engaging portion provided that the proximal end of the stent is disposed within the outer sheath; and the stent-retention element is operable to withdraw the stent proximally back into the outer sheath provided that a proximal portion of the stent is disposed within the outer sheath.

Some embodiments of the present stent advancement methods include advancing a stent disposed within a sheath disposed within a body vessel using a multiple reciprocating movements of a reciprocating element, where: each reciprocating movement includes a distal movement of the reciprocating element and a proximal movement of the reciprocating element; the stent is advanced distally in response to each distal movement of the reciprocating element; the stent is not advanced in response to each proximal movement of the reciprocating element; and each distal movement of the reciprocating element does not coincide with a separate proximal movement of the sheath.

Some embodiments of the present stent advancement methods include distally driving a stent out of a sheath and into a tubular structure by repeatedly engaging the stent between its distal and proximal ends with a stent-engaging element, where at least two of the engagements are separated by a period of non-engagement; and as the stent is distally driven out of the sheath, varying the axial density of the stent within the tubular structure by varying the axial position of the sheath relative to the tubular structure.

Some embodiments of the present stent advancement instruction methods include instructing a person on how to use a stent delivery device that includes a sheath and a stent disposed in the sheath, the instructing including demonstrating the following steps to the person: distally driving the stent out of the sheath and into a tubular structure by repeatedly engaging the stent between its distal and proximal ends with a stent-engaging element, where at least two of the engagements are separated by a period of non-engagement; and as the stent is distally driven out of the sheath, varying the axial density of the stent within the tubular structure by varying the axial position of the sheath relative to the tubular structure.

Any embodiment of any of the present devices and methods may consist of or consist essentially of—rather than comprise/include/contain/have—the described features and/or steps.

Details associated with these embodiments and others are provided below.

BRIEF DESCRIPTION OF THE DRAWINGS

The following drawings illustrate by way of example and not limitation. They illustrate two different embodiments of the present delivery devices, the second of which appears in FIGS. 13 and 14. They also illustrate the manner in which stent density can be altered during delivery (FIGS. 15A-15C), and a schematic of one of the present demonstration techniques (FIG. 16).

FIGS. 1, 2A, 2B, 2C, 3A, 3B, 3D, 3E, 4-7, 11, 12A, 13, and 14 are drawn to scale (in terms of proportions), save the length of line 72, which can be varied as desired. Identical reference numerals do not necessarily indicate an identical structure. Rather, the same reference numeral may be used to indicate a similar feature or a feature with similar functionality. Not every feature of each embodiment is labeled in every figure in which that embodiment appears, in order to keep the figures clear.

FIG. 2D is a cross-sectional view of a sub-assembly of an embodiment of device.

FIG. 9 depicts stent in a constrained, or elongated, configuration.

FIG. 10 shows stent in an expanded state in body vessel.

FIG. 12B shows an embodiment of stent-retention element.

DESCRIPTION OF ILLUSTRATIVE EMBODIMENTS

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device or method that "comprises," "has," "contains," or "includes" one or more elements possesses those one or more elements, but is not limited to possessing only those one or more elements or steps. Likewise, an element of a device or a step of a method that "comprises," "has," "contains," or "includes" one or more features possesses those one or more features, but is not limited to possessing only those one or more features. Furthermore, a structure that is configured in a certain way must be configured in at least that way, but also may be configured in a way or ways that are not specified.

Any embodiment of any of the present devices and methods may consist of or consist essentially of—rather than comprise/include/contain/have—the described features and/or steps.

The terms "a" and "an" are defined as one or more than one unless this disclosure explicitly requires otherwise. The terms "substantially" and "about" are defined as at least close to (and include) a given value or state (preferably within 10% of, more preferably within 1% of, and most preferably within 0.1% of).

An illustrative embodiment of the present devices appears in perspective in FIG. 1. Device 10 includes outer sheath 20 and device body 90 (which, in this embodiment, is a handle configured to be held in one hand) coupled to outer sheath 20. In this embodiment, the outer sheath is coupled to the handle such that the outer sheath cannot move relative to the handle (that is, the two are coupled to each other in a fixed relationship). Outer sheath 20 is a hollow member configured such that a stent can be disposed within it when the stent is in a constrained (e.g., elongated) state prior to delivery.

Figure 2C:
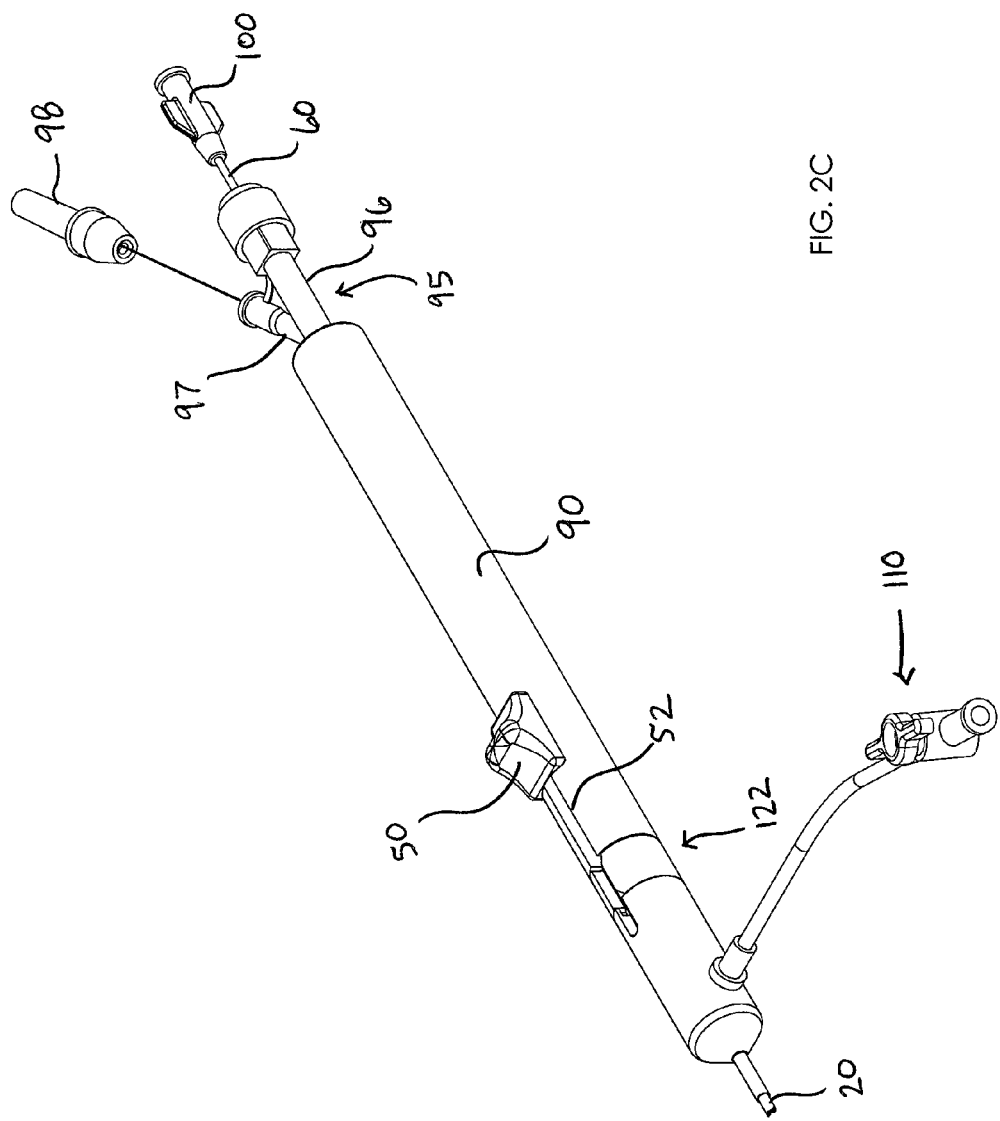
Figure 3A:
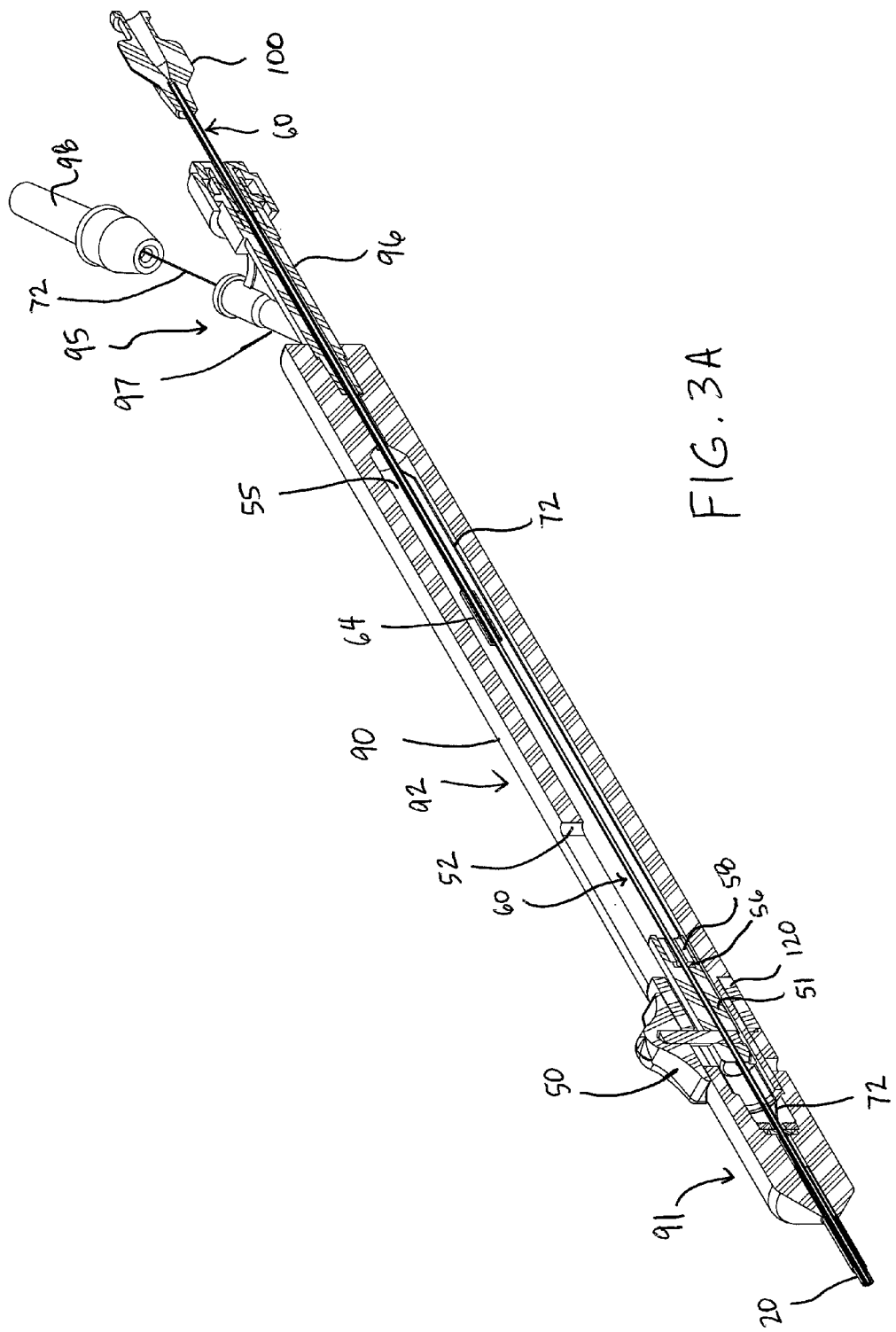

A portion of the embodiment of FIG. 1 near device body 90 is illustrated in perspective in FIG. 2A and in cross-section in FIG. 3. These figures show that device 10 includes user-actuatable element 50 that is coupled to (and, in this embodiment, mounted on so as to be slidable with respect to) device body 90 and also coupled to element 40, which in this embodiment has a passageway and is configured to fit within outer sheath 20. In the embodiment shown in FIGS. 2A and 3A, user-actuatable element 50 is slidably mounted on device body 90 and coupled to element 40 via block 51. In some embodiments, block 51 may include a biasing element (such as a spring) that biases user-actuatable element 50 toward the position shown in FIG. 3A. In other embodiments, block 51 does not include a biasing element.

User-actuatable element 50, block 51, and element 40 of device 10 are moveable in the proximal and distal directions (which is along the longitudinal axis (not shown) of the device), and are generally constrained in other directions. Thus, proximal movement of user-actuatable element 50 (towards proximal side 92) results in proximal movement of element 40, and distal movement of user-actuatable element 50 (towards distal side 91) results in distal movement of element 40. In the depicted embodiment, the distance that user-actuatable element 50 moves (either proximally or distally) will translate into movement of element 40 by the same distance. This translation could be geared up or down as desired. As explained in greater detail below, element 40 is coupled to stent-engaging element 45, which engages and drives the loaded stent distally from the outer sheath during at least a portion of the time the stent-engaging element is moved distally within the lumen of the stent.

FIG. 2A also shows that device 10 may include an element 25 that is coupled (slidably) to the outside of outer sheath 20. Element 25 can be configured to slide relatively freely along the outer surface of the outer sheath, and it can be configured to interface with a hemostasis valve of an introducer (see FIG. 3B). Specifically, in can be configured to fit partially inside the introducer and interface with the hemostasis valve such that fluid does not flow back toward the handle of the device yet the outer sheath of the device can slide relatively freely within element 20 and the introducer. Effectively, element 25 can act to reduce the friction between the outer sheath of the device and an introducer through which the outer sheath of the device is inserted, while maintaining a substantial fluid seal between the outer sheath and the exterior of the patient.

Figure 5:
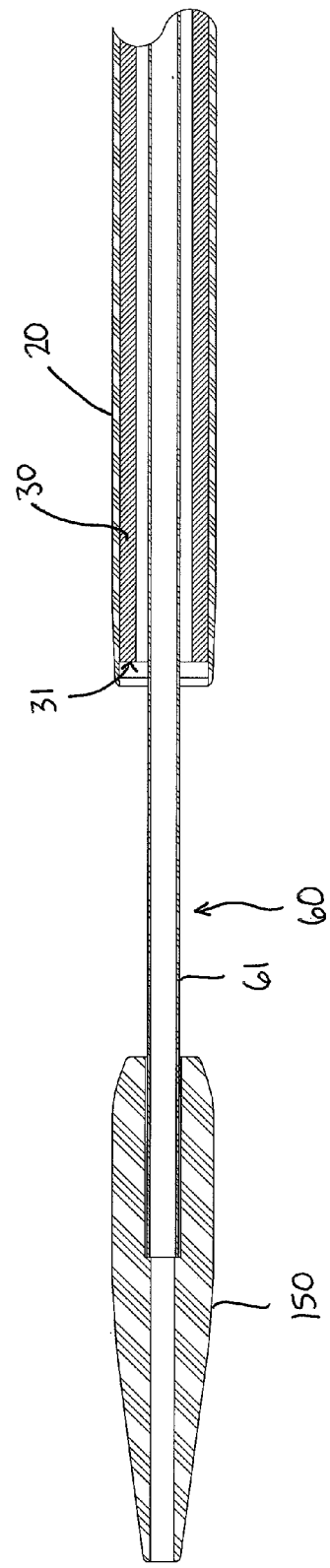

Referring to FIGS. 1, 4 and 5, outer sheath 20 extends distally from device body 90. Device 10 also includes inner element 60, a portion of which is located within outer sheath 20. Inner element 60 (and, more specifically in the preferred embodiment, inner sleeve 61 as shown in FIG. 2D, described below) is coupled at its distal end to nose cone 150. Inner element 60, which is not constrained axially by sheath 20 (in that the two have sufficiently different diameters that they do not touch), facilitates motion of nose cone 150 relative to outer sheath 20 and it is sized such that a guidewire may be passed through it (as is nose cone 150). Radiopaque marker 27 may be placed at any suitable location along outer sheath 20 in order to provide a means for aiding deployment of a stent. For example, the distance from the distal end of outer sheath 20 and marker 27 may be the nominal length of the stent being delivered in its deployed state. FIG. 5 illustrates distal end 31 of stent 30 within outer sheath 20. In some embodiments, neither element 40 nor stent-engaging element 45 is attached to inner element 60. As a result, element 40 may be moved proximally and over inner element 60 while inner element 60 is stationary. Similarly, stent-engaging element 45 may be moved proximally and distally over inner element 60 while inner element 60 is stationary.

Returning to FIGS. 2A and 3A and referring also to FIG. 2C, the allowable proximal-distal travel of user-actuatable element 50 is constrained by the length of slot 52 in device body 90, as well the position of stopper 120. First position 121 of stopper 120 shown in FIG. 2A limits the distal travel of user-actuatable element 50 to less than the full length of slot 52. Preferably, first position 121 corresponds to a distal-most position of user-actuatable element 50 where the stent-engaging element 45 remains within outer sheath 20. This corresponds to the proper configuration for advancement of stent 30. Stopper 120 is preferably biased to first position 121 with, e.g, a spring. In FIGS. 2C and 3A, stopper 120 has been rotated to a second position 122 (labeled as such in FIG. 2C) that allows user-actuatable element 50 to slide past it, as shown.

FIG. 2D is a cross-sectional view of a sub-assembly of a preferred embodiment of device 10, which sub-assembly includes a preferred embodiment of inner element 60 in the form of an inner sleeve 61 that extends the length of inner element 60 and that is configured to accept a guidewire. Inner element 60 may also include intermediate sleeve 62 that may be secured at its distal end (or any other suitable location) to inner sleeve 61 in any suitable fashion, such as Loctite® 4014 adhesive. Intermediate sleeve 62 (which may be a hypotube) also may extend to the proximal end of inner element 60. Inner element 60 may also include outer sleeve 63 (which may be a hypotube) connected at its distal end (or any other suitable location) to intermediate sleeve 62 in any suitable manner, such as through soldering; outer sleeve 63 also may extend to the proximal end of inner element 60. Inner element 60 may also include a travel-limiting sleeve 64 connected at its distal end (or any other suitable location) to outer sleeve 63 in any suitable fashion, such as through soldering. Sleeve 64 may be configured to restrict the travel of inner element 60 with respect to device body 90. More specifically, sleeve 64 can be configured to interfere (due to its size) with the proximal opening (not labeled) of cavity 55 of device body 90 (see FIG. 3A), and it can be configured to interfere distally with block 51 (if Luer fitting 100 does not first interfere with Y-adapter 95).

Figure 3B:
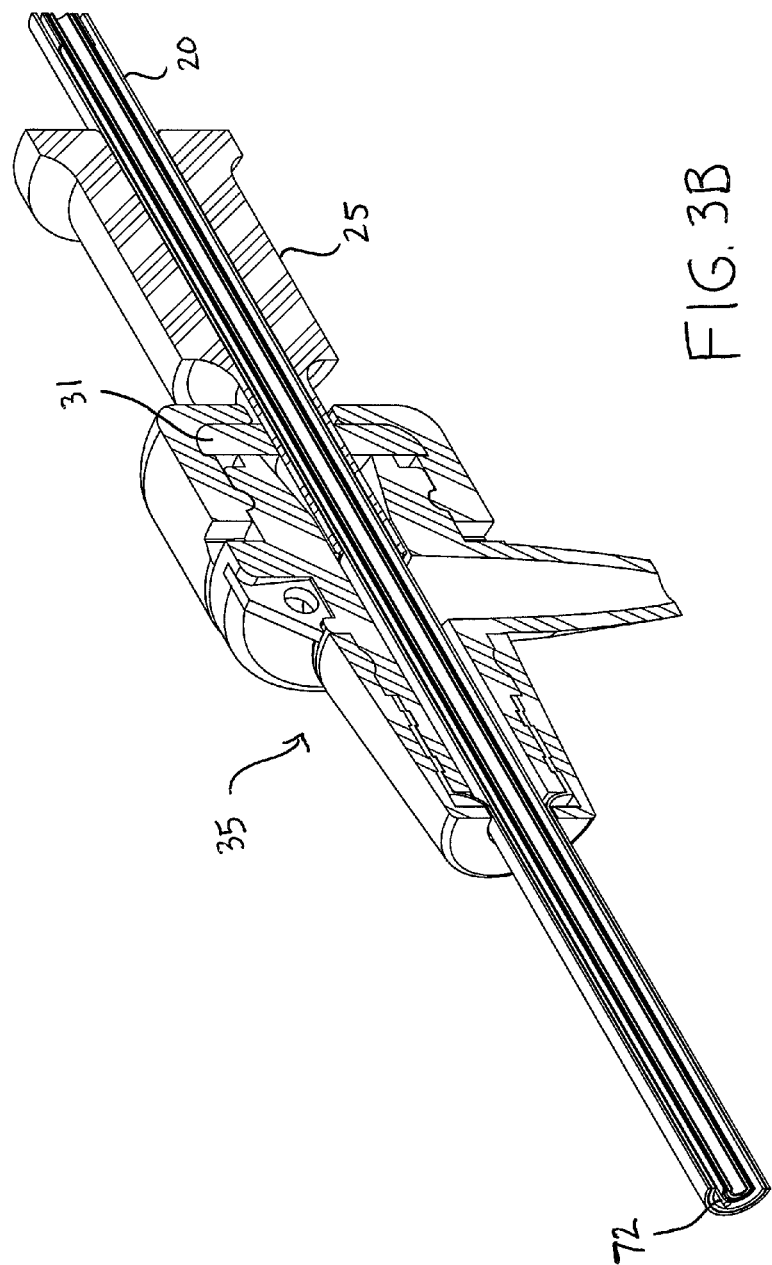

FIG. 3B is an enlarged, cross-sectional view, showing the interaction between element 25 and introducer 35, where element 25 is interfacing with seal 31 of the hemostasis valve of introducer 35.

Figure 3C:
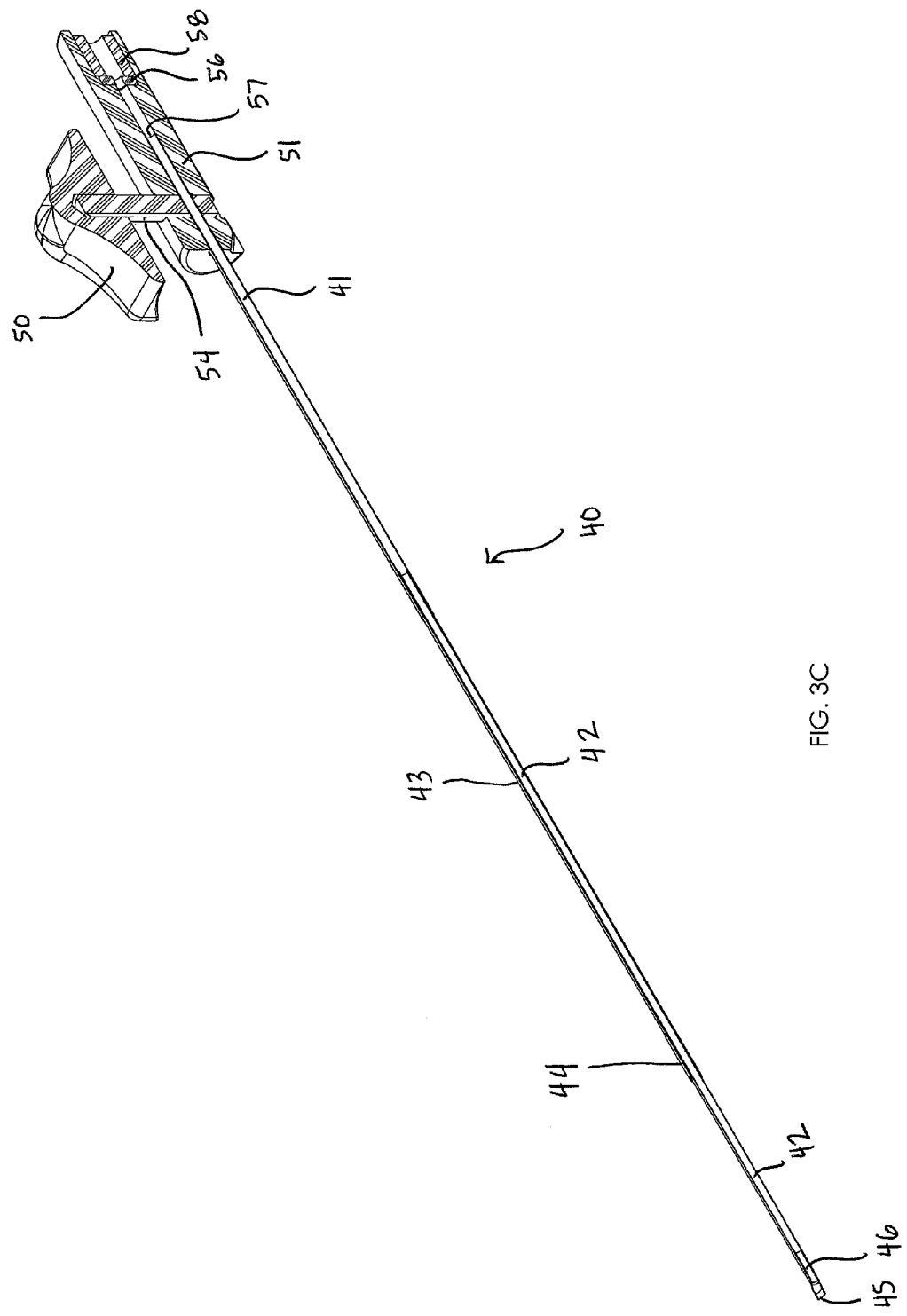
FIG. 3C is a cross-sectional view of a sub-assembly of an embodiment of device.

FIG. 3C is a cross-sectional view of a sub-assembly of a preferred embodiment of device 10, which sub-assembly includes a preferred embodiment of element 40 in the form of proximal hypotube 41 secured in any suitable fashion to block 51, such as by a press fit that terminates at shoulder 57 or with a suitable adhesive, such as one of the Loctite® adhesives (e.g., 4014, 4305, 3321, etc.). Block 51 is secured to user-actuatable element 50 through pin 54, which can be bonded to element 50 and press fit or bonded to block 51. Element 40 may also include an intermediate tube 42 that is connected at its proximal end to proximal hypotube 41 in any suitable manner, such as through Loctite® 4305, and at its distal end to support tube 46 (that is in turn connected to stent-engaging element 45 in any suitable fashion, such as an adhesive) in any suitable manner, such as through an adhesive. Element 40 may also include a support tube 43 that is positioned over intermediate tube 42 and that abuts the distal end of proximal hypotube 41. Support tube 43 may be connected at any suitable location to intermediate tube 42 using any suitable adhesive. The support tube may be configured to increase the rigidity of intermediate tube 42. Element 40 may also include resheathing stop 44 that is threaded over intermediate tube 42 and that abuts the distal end of support tube 43. Resheathing stop 44 may be connected at any suitable location to intermediate tube 42 using any suitable adhesive. Resheathing stop 44 may be configured to prevent proximal movement of the stent that is enclosed by outer sheath 20 (not shown in this figure) should the stent be re-sheathed during the delivery process. The depicted sub-assembly also includes a silicone seal 56 that is designed to prevent the backflow of fluid around the outside of inner element 60 (and, more specifically, an outer hypotube that is part of a preferred embodiment of inner element 60) and that is held in place by a stainless steel retainer 58.

Figure 6:
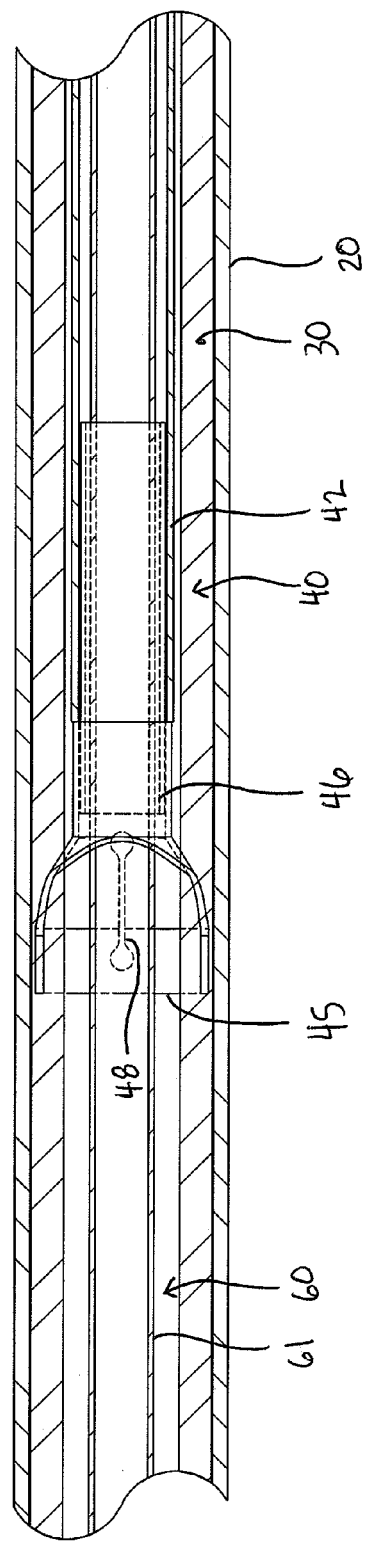

Referring to FIG. 6, element 40 extends such that a portion of it is located within outer sheath 20. Preferably, element 40 is hollow and its passageway accommodates a portion of inner tube 60 being located within it. Alternate embodiments of this element may be non-hollow.

Figure 7:
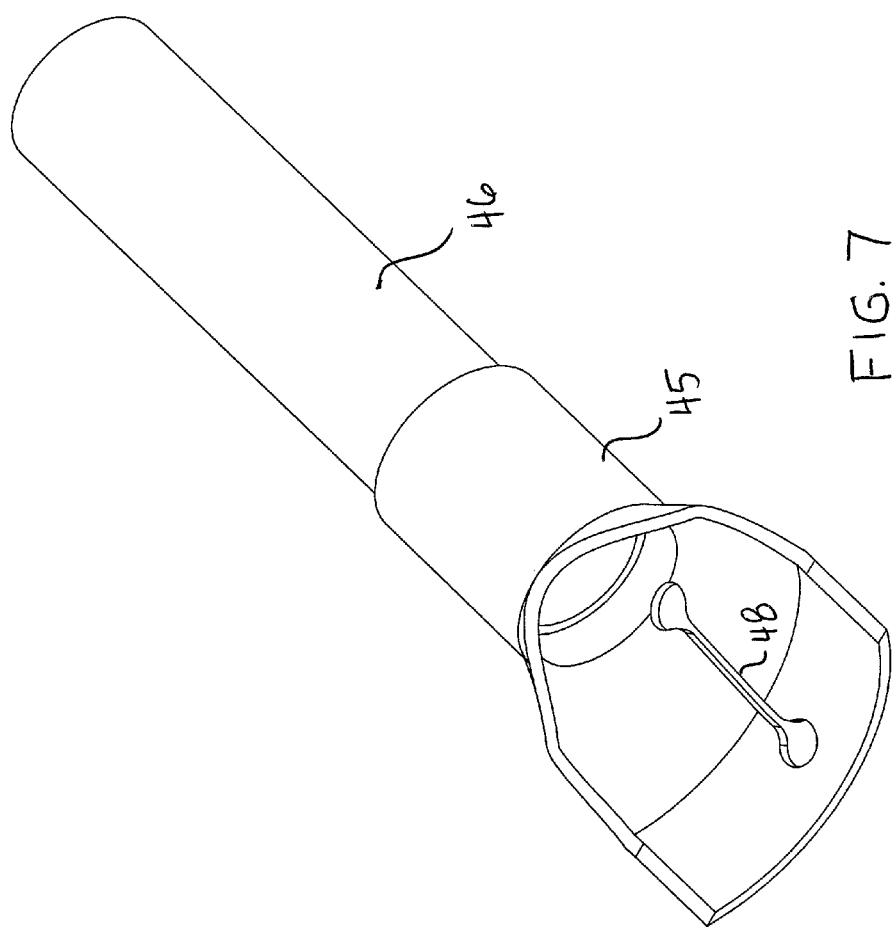

Referring to FIGS. 6-7, element 40 is coupled to a stent-engaging element 45, which, in this embodiment, is shaped like a shovel or scoop. More specifically, in the depicted preferred embodiment, intermediate tube 42 of element 40 is connected to support tube 46, which is connected to stent-engaging element 45. Stent-engaging element 45 is positioned at least partially within the lumen of stent 30. As element 40 moves distally in response to distal movement of user-actuatable element 50, stent-engaging element 45 engages stent 30, advancing it along outer sheath 20. In a preferred embodiment, proximal motion of stent-engaging portion 45 results in no motion of stent 30. Repeated reciprocating distal and proximal motion of element 40 in this manner results in advancement of stent 30 until it exits outer sheath 20. Thus, those of ordinary skill in the art will understand that the illustrated embodiment of device 10 is configured such that a user can advance stent 30 distally out of outer sheath 20 through multiple engagements of the stent by stent-engaging element 45, where each engagement: occurs between the proximal and distal ends of stent 30, drives stent 30 distally without a mechanized concomitant withdrawal of outer sheath 20, and is separated from any subsequent engagement by a period of not driving stent 30 distally; and the user's proximal-most point of contact with device 10 that causes each engagement (which occurs at user-actuatable element 50) is located at or distal of the proximal end of device body 90. Stent-engaging element 45 may include a flex slot 48 provided with rounded, dumbbell-shaped ends that help alleviate fatigue stress fractures and the like and that allow element 45 to fold inwardly as it slides proximally within the lumen of stent 30. Preferably, the performance of stent-engaging portion 45 is achieved by appropriate shape selection, as depicted in FIG. 7. Alternate embodiments may employ stent-engaging portions that flex, are hinged, or otherwise change shape to achieve stent advancement. The configuration of the stent-engaging portion may be chosen to best suit the type of stent to be deployed. When stent 30 is a woven, self-expanding stent, such as the kind disclosed in U.S. Pat. No. 7,018,401, which is incorporated by reference, stent-engaging element 45 is preferably configured (as shown in the figures) so as to (a) engage wire intersections on opposing sides of stent 30 when driving the stent distally, and (b) fold inwardly (due, at least in part, to flex slot 48 of the stent-engaging element) and slide proximally within the stent's lumen.

Figure 8:
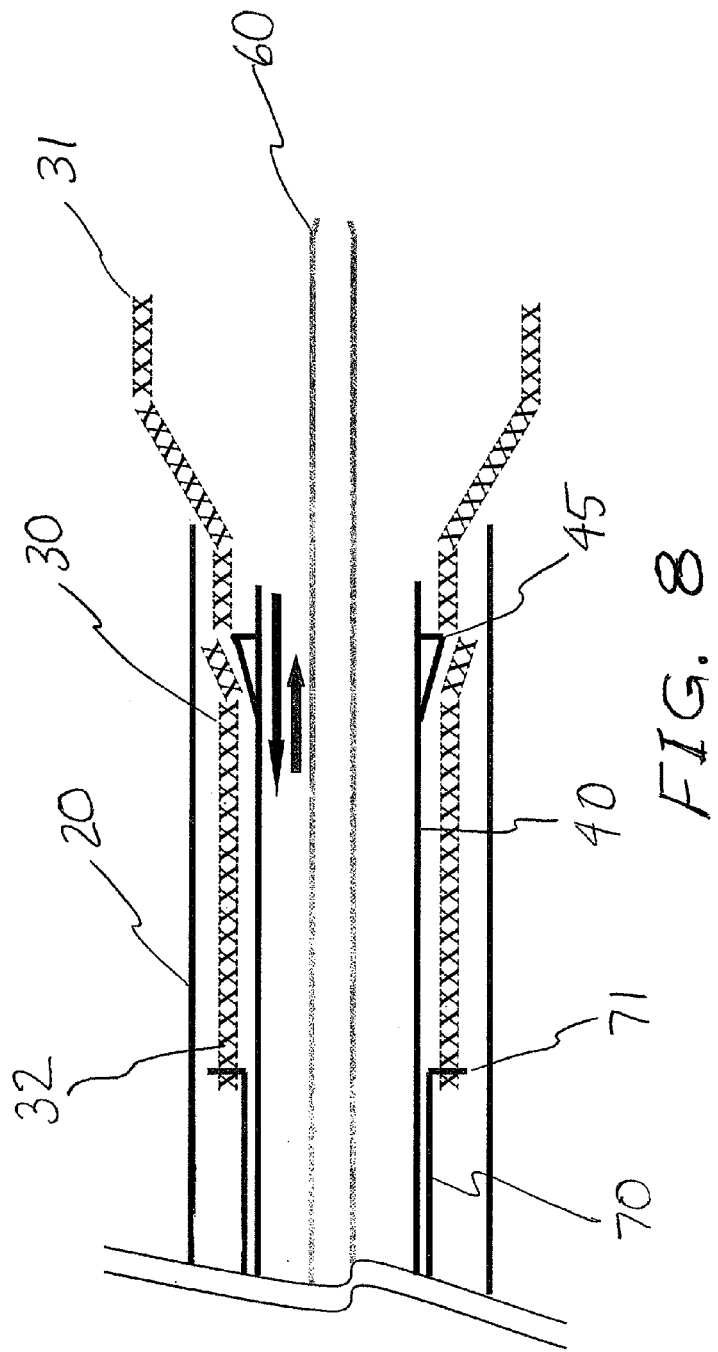
FIG. 8 provides a schematic depiction of the stent advancement process.

FIG. 8 provides a schematic depiction of the stent advancement process. Distal end 31 of stent 30 has exited outer sheath 20 and has expanded. Element 40 moves proximally and distally, as indicated by arrows. As stent-engaging element 45 travels distally, it engages and advances stent 30, thus driving it out of outer sheath 20. No advancement of stent 30 occurs when stent-engaging element 45 travels proximally due to the shape of stent-engaging element 45. Instead, the configuration of stent-engaging element 45 enables it to bend inwardly as it moves over and encounters portions (e.g., wire portions) of stent 30 during the proximal movement of user-actuatable element 50 without disturbing the axial position of the stent relative to the outer sheath. Preferably, advancement of stent 30 is achieved without a mechanized concomitant withdrawal of outer sheath 20 and without motion of outer sheath 20 relative to device body 90 (aside from incidental motion caused by patient's body movements, vibrations, etc.).

FIGS. 9-10 illustrate schematically stent deployment in a body vessel. FIG. 9 depicts stent 30 in a constrained, or elongated, configuration. This is an example of a configuration of stent 30 when it is within outer sheath 20 of device 10. FIG. 10 shows stent 30 in an expanded state in body vessel 160, which is one state a self-expanding stent may take when it exits outer sheath 20.

Figure 11:
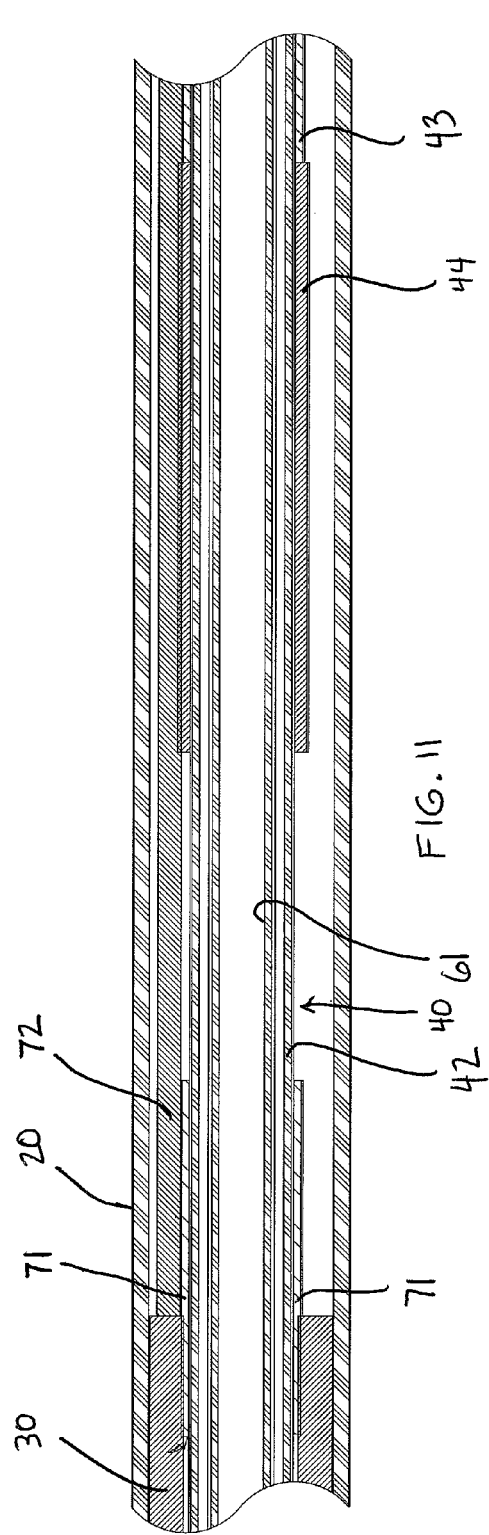
Figure 12A:
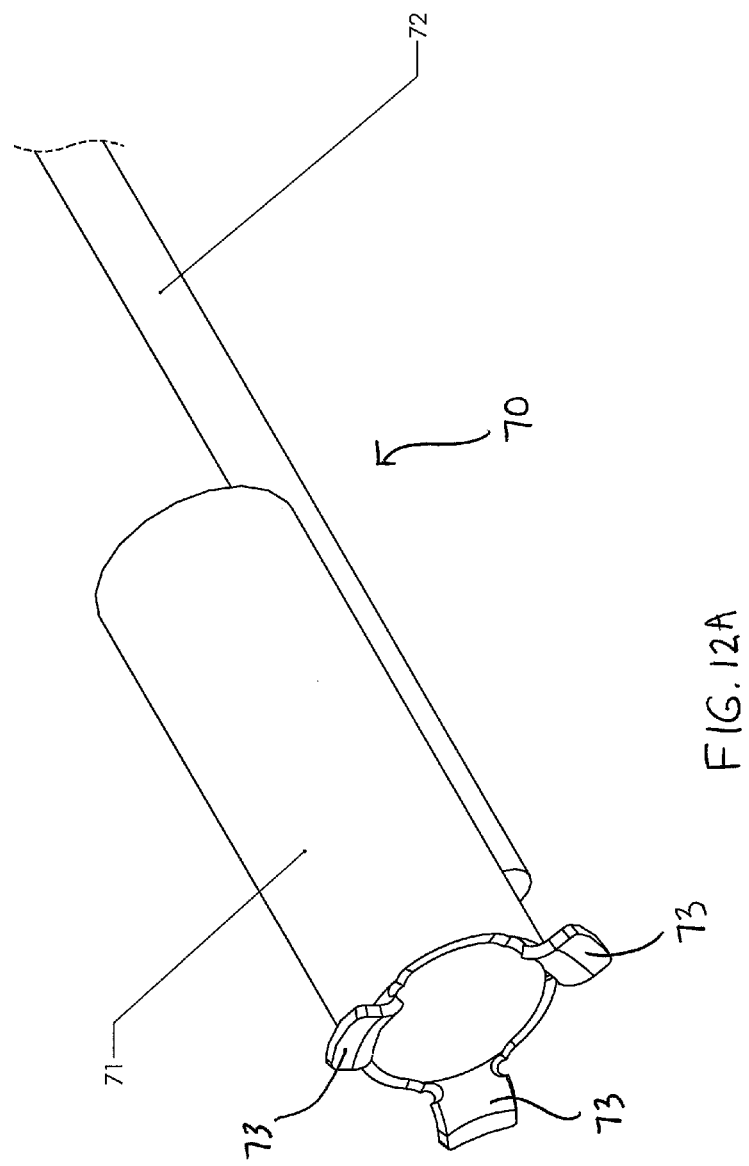

In some embodiments, the present devices may also include a stent-retention element configured to allow an operator to re-sheath the stent during the advancement and/or deployment process, provided the stent has not been advanced completely out of the sheath. Referring to FIGS. 11 and 12A, device 10 includes stent-retention element 70 coupled to proximal end 32 of stent 30. In a preferred embodiment, contact between distal portion 71 of stent-retention element 70 and stent 30 exists as long as proximal end 32 of stent 30 is within outer sheath 20, even during proximal movement of stent-engaging element 45. When proximal end 32 of stent 30 is advanced outside of outer sheath 20, stent 30 expands to a radius larger than the greatest width (taken in the radial direction shown in the figures) of distal portion 71 of stent-retention element 70. As a result, contact between stent 30 and stent-retention element 70 ceases, and deployment of stent 30 is completed. Accordingly, stent-retention element 70 is operable to withdraw stent 30 proximally back into outer sheath 20 (through action by an operator) provided that a proximal portion of stent 30 (specifically, the proximal portion coupled to stent-retention element 70) is disposed within outer sheath 20.

Referring to FIGS. 2A, 3A and 11-12, proximal portion 72 (also visible in FIG. 3B) of stent-retention element 70 is a cable or similar device that facilitates withdrawal of stent 30 proximally back into outer sheath 20 and that may be characterized as a stent-retention line, provided that a proximal portion of stent 30 is disposed within outer sheath 20. Distal portion 71 of stent-retention element 70 may be a piece of tubing (such as hypotube) that is provided with multiple, radially-projecting prongs 73 that engage openings in woven versions of stent 30. The tubing may be coupled in any suitable fashion (such as through soldering) to proximal portion 72.

As shown in FIGS. 1 and 2A, Y-adapter 95 may be coupled to the proximal portion of device body 90. Inner tube 60 may be placed through straight arm 96 and proximal portion 72 may be placed through angled arm 97 of Y-adapter 95. As shown in FIG. 2B, a stent-retention element position marker 93 may be coupled to line 72 and positioned along the line to the relative position of the stent that is coupled to the stent-retention element. For example, the marker, which may be a piece of heat shrink tubing, may be positioned along the line such that when it extends into the perimeter of angled arm 97 the stent will completely exit outer sheath 20. In this way, an operator has a visual indicator that conveys how far the stent has exited the outer sheath. FIGS. 1 and 2A also show that the stent-retention element may include a finger element 98 coupled to line 72 in any suitable manner (e.g., though LOCTITE® adhesive), to provide a user with something to hold to enable manipulation of the stent-retention element. FIG. 12B shows a preferred embodiment of stent-retention element 70, which finger element 98 in cross-section and showing an example connection location 99 (for adhesive or the like) between line 72 and finger element 98 (which may have inner and outer components, as shown, that are threaded together).

Preferably, device 10 comprises side port 110 (coupled to device body 90) and Luer fitting 100 (coupled to proximal end 62 of inner tube 60) to allow for flushing of outer sheath 20 and inner tube 60, respectively. The flushing may be with saline and may occur prior to a procedure. Alternate embodiments of the present devices may include alternate designs for flushing outer sheath 20 and inner tube 60, or may not be configured to allow for flushing. FIG. 3D is a top view of device 10 and identifies a cutaway detail near the distal end of device body 90 that is shown in greater detail in FIG. 3E.

Referring to FIG. 2C, second position 122 of stopper 120 allows user-actuatable element 50 to travel distally the full length of slot 52. The distal-most position of user-actuatable element 50 corresponds to a position where stent-engaging element 45 is outside (distal to) outer sheath 20, and therefore in a region where stent 30 will be driven out of outer sheath 20 and in its expanded state. A stent in this position that is de-coupled from distal portion 71 of stent-retention element 70 can no longer be withdrawn into outer sheath 20. Furthermore, a stent in an expanded condition will have radial clearance over stent-engaging element 45. Alternate embodiments of the present devices may employ other designs to limit the travel of user-actuatable element 50, or have no adjustable travel-limiting feature.

Figure 14:
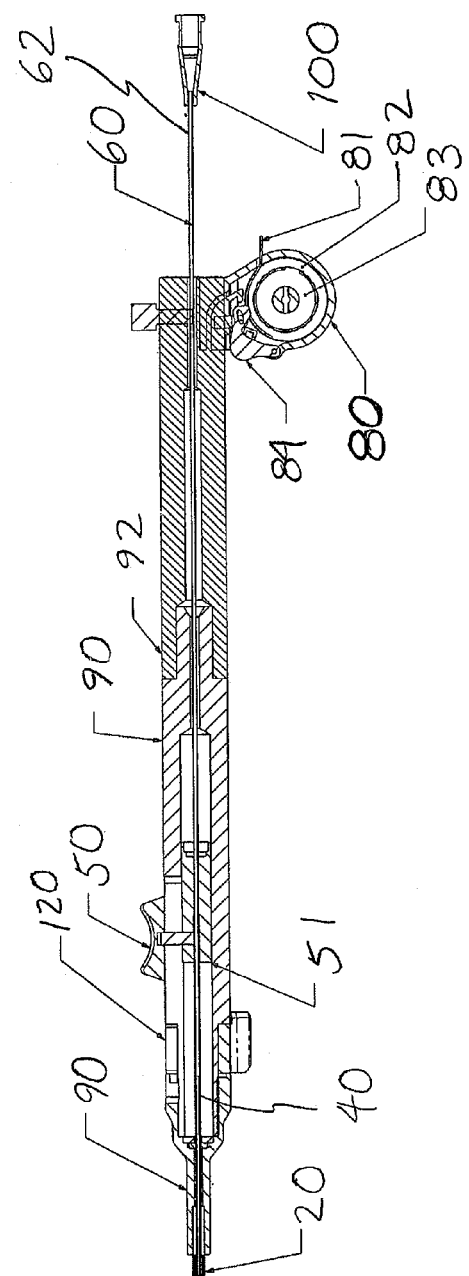

FIGS. 13-14 depict another embodiment of the present devices that includes capture device 80 coupled to proximal portion 72 of stent-retention element 70. Capture device 80 serves to release appropriate amounts of proximal portion 72 as stent-engaging element 45 advances stent 30. Capture device 80 includes a stop that serves to halt distal advancement of stent 30 prior to full deployment of stent 30 from outer sheath 20. The stop (which can be a piece of tubing, such as hypotube, that is coupled at an appropriate location to proximal portion 72) provides operator feedback at the point where further advancement would result in stent deployment (thus, the stop can be used as an indicator of the location at which stent withdrawal will no longer be possible). Here, the operator may choose to withdraw stent 30 into outer sheath 20 for repositioning by pulling proximally on stent-retention element 70, or proceed with stent deployment by depressing deployment stop lever 81 (which allows the stop to bypass the deployment stop lever and permits continued distal advancement of the stent-retention element) and continuing with advancement via user-actuatable element 50.

If the operator chooses to withdraw stent 30 into outer sheath 20 for repositioning, the operator can actuate retention pull lever 84, which (in the depicted embodiment) de-couples capture device 80 from device body 90 and allows the operator to proceed with drawing stent 30 by pulling proximal portion 72 of stent-retention element 70 proximally. After withdrawal of stent 30 into outer sheath 20, retention pulley 82 and spring 83 of capture device 80 operate to accumulate excess slack of stent-retention element 70. In this embodiment, proximal portion 72 of stent-retention element 70 may be threaded through a portion of device body 90 that is not centrally disposed within the device body. Alternate embodiments of the present devices that include capture devices may include capture devices that are configured differently from capture device 80, such as automated capture devices. Furthermore, capture device 80 may be coupled to angled arm 97 in the embodiment of device 10 shown in FIG. 1, in place of finger element 98.

The present devices may be disposable and packaged in a bag, pouch, box, or other suitable container, after having been sterilized using any suitable technique, such as sterilization using ethylene oxide gas. There may be a small gap between the distal end of the outer sheath and the proximal end of the nose cone to allow for the sterilizing gas to flow throughout the device. The container may include instructions for using the device that are printed on the container or included inside the container. After the device is removed from its container, saline may be used to flush the outer sheath and its contents and the inner tube. The gap between the nose cone and the outer sheath can then be closed by pulling proximally on the inner tube to which the nose cone is coupled. If the procedure involves stenting a blood vessel, any suitable technique for positioning the device in the appropriate location may be used (e.g, such as the Seldinger technique). The nose cone of the device (which may be any suitable flexible tip) may be radio opaque and may represent a distal-most marker for the device. Another radio opaque marker made from any suitable material (such as a platinum band, or a band made from any suitable platinum alloy) may be coupled to a portion of the device that is proximal to the nose cone, such as to the outer sheath (as discussed above), element 40, or the inner element, to create a proximal-most marker for the device. These two markers may be used by the operator to position the device relative to the lesion of interest to enable accurate deployment of the stent.

The present methods include stent advancement methods for distally driving a stent out of a sheath (e.g., outer sheath 20) and into a tubular structure. In some embodiments, the tubular structure is animal tissue (such as a human blood vessel). In other embodiments, the tubular structure is not animal tissue and comprises a polymer structure that can be used to test a given device technique or demonstrate stent advancement to one or more persons, such as a doctor considering using the device or stent advancement technique in his or her practice.

Some embodiments of the present stent advancement methods include distally driving a stent (e.g., stent 30) out of a sheath (e.g., outer sheath 20) and into a tubular structure by repeatedly engaging the stent between its distal and proximal ends with a stent-engaging element (e.g., stent-engaging element 45), where at least two of the engagements are separated by a period of non-engagement; and as the stent is distally driven out of the sheath, varying the axial density of the stent within the tubular structure by varying the axial position of the sheath relative to the tubular structure. As the stent is driven distally out of the sheath, the remainder of the device is withdrawn proximally by the operator relative to the tubular structure so that the deployed portion of the stent remains stationary relative to the tubular structure (e.g., human tissue) into which it is deployed. The rate at which the remainder of the device is withdrawn may be varied to vary the axial density of the stent: a slower withdrawal rate increases the axial density of the stent, whereas a faster rate decreases the axial density of the stent. It may be desirable to increase the axial density of the stent in, for example, a location where a greater hoop strength is required to maintain the patency of the tubular structure, such as along a stenosed region 210 of an artery 200 as shown in FIG. 15A. It may be desirable to decrease the axial density of the stent in, for example, a location where fluid flow into a section of the stent from the side is anticipated or desired, or at the location of penetration of a second stent, either of which may be true at an anatomical side branch 260 of a vessel 250 as shown in FIG. 15B.

Some embodiments of the present stent advancement methods include distally driving a stent (e.g., stent 30) out of a sheath (e.g., outer sheath 20) and into a tubular structure by repeatedly engaging the stent between its distal and proximal ends with a stent-engaging element (e.g., stent-engaging element 45), where at least two of the engagements are separated by a period of non-engagement; and engaging the stent at its proximal end with a stent-retention element (e.g., stent-retention element 70) that is positioned within the sheath.

In some embodiments, the engagements that drive the stent distally from the sheath may be achieved using a device that is configured to not mechanically concomitantly withdraw the sheath as the stent is driven distally, such as the versions of the present devices shown in the figures. The tubular structure in those embodiments can be an anatomical tubular structure, such as a vessel or duct, or a tubular structure that is not animal tissue, such as a polymer tube 300 (see FIG. 15C). Regardless, in some embodiments, the method may also include engaging the stent at its proximal end with a stent-retention element that is positioned within the sheath. The stent-retention element may include a stent-retention line, and the method may also include, after the stent is partially-driven out of the sheath, withdrawing the stent back into the sheath by moving the stent-retention line. An operator may accomplish the driving of the stent by moving a user-actuatable element (e.g., user-actuatable element 50) with the operator's thumb. The stent may be woven, a stent-engaging element may engage multiple wire intersections of the stent and move distally during the engagements that drive the stent, and the stent-engaging element may slide proximally within the stent's lumen during the period of non-engagement.

Some of the present methods are methods of instructing another or others on how to advance a stent out of sheath and into a tubular structure. Some embodiments of the present stent advancement instruction methods include instructing a person on how to use a stent delivery device (e.g., device 10)

that includes a sheath (e.g., outer sheath 20) and a stent (e.g., stent 30) disposed in the sheath. The instructing may include demonstrating the following steps to the person: distally driving the stent out of the sheath and into a tubular structure by repeatedly engaging the stent between its distal and proximal ends with a stent-engaging element (e.g., stent-engaging element 45), where at least two of the engagements are separated by a period of non-engagement; and, as the stent is distally driven out of the sheath, varying the axial density of the stent within the tubular structure by varying the axial position of the sheath relative to the tubular structure.

Some embodiments of the present stent advancement instruction methods include instructing a person on how to use a stent delivery device (e.g., device 10) that includes a sheath (e.g., outer sheath 20) and a stent (e.g., stent 30) disposed in the sheath. The instructing may include demonstrating the following steps to the person: distally driving the stent out of the sheath and into a tubular structure by repeatedly engaging the stent between its distal and proximal ends with a stent-engaging element (e.g., stent-engaging element 45), where at least two of the engagements are separated by a period of non-engagement; and engaging the stent at its proximal end with a stent-retention element (e.g., stent-retention element 70) that is positioned within the sheath.

Figure 16:
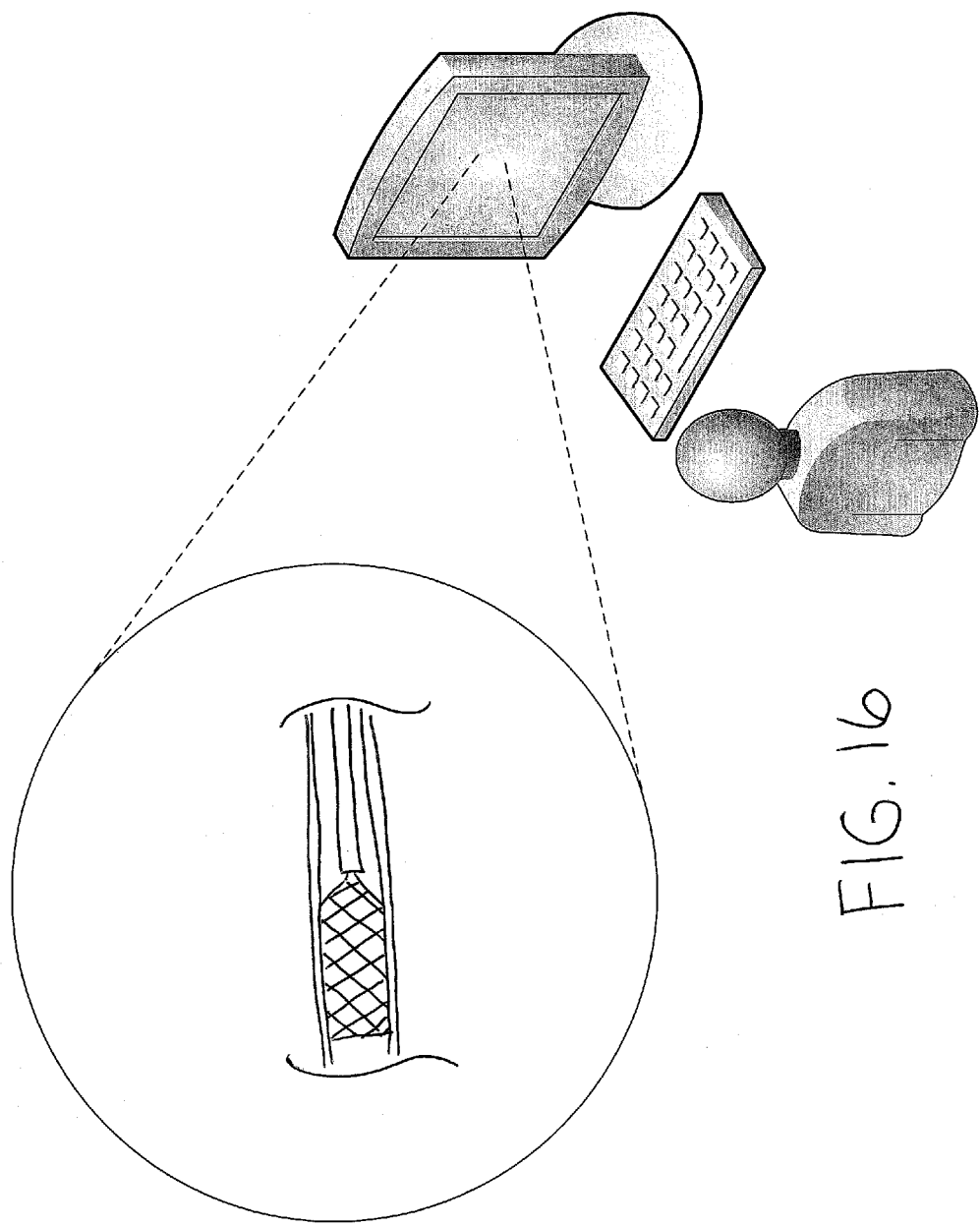

The instruction methods may be accomplished in some embodiments by a live demonstration in the presence of the person and in other embodiments by a recorded or simulated demonstration that is played for the person. An example of a recorded demonstration is one that was carried out by a person and captured on camera. An example of a simulated demonstration is one that did not actually occur, and that instead was generated using a computer system and a graphics program. In the case of a recorded or simulated demonstration, the demonstration may exist in any suitable form—such as a on DVD or in any suitable video file (such as an mpg, .mov., .qt, .rm, .swf, or .wmv file)—and the instructing may be accomplished by playing the demonstration for the viewer using any suitable computer system. The viewer or viewers may cause the demonstration to play. For example, the viewer may access the recorded or simulated demonstration file using the internet, or any suitable computer system that provides the viewer with access to the file. See FIG. 16.

In embodiments of the present methods that involve stent delivery into an anatomical structure, and the device used to accomplish the method is in a desired location within a patient to start the stent advancement, the movement (e.g, the ratcheting movement) of the stent-engagement element can begin such that the distal end of the stent (which can also be provided with one or more radio opaque markers to enable easier viewing of its position during the procedure) exits the outer sheath of the device, but not to such an extent that it expands to contact the anatomical structure. If the distal end of the stent is proximal of where the operator wants it, and a stent-retention element is used, the stent-retention element can be pulled proximally to resheath the stent and reposition the device; if the stent is distal of where the operator wants it, the entire device can be withdrawn proximally and the deployment process continued.

The different features of the present devices can be made from commercially-available, medical-grade materials. For example, nose cone 150 may be made from a polyether block amide (such as PEBAX® resin, available from Arkema Inc, Philadelphia, Pa.). A distal portion of inner element 60 (such as inner sleeve 61) may be made from polyimide and coupled to a more proximal portion made from stainless steel hypotube (such as 304 or 316L stainless steel). Luer fitting 100 coupled to inner element 60 (e.g., outer sleeve 63) may be made from polycarbonate. Outer sheath 20 may be made from a braided polyether block amide (e.g, a braided PEBAX® resin). Device body 90, user-actuatable element 50, block 51, and stopper 120 may be made from ABS (acrylonitrile butadiene styrene) plastic, polycarbonate, or DELRIN® acetal resin (available from DuPont). Stopper 120 may be coupled to a stainless steel spring that biases it as described above. Element 40 may have a shaft formed from polyimide (or, a series of shafts, as in the preferred embodiment, that are made from polyimide or nitinol hypotube), and stent-engaging element 45 may include or be coupled to a short piece of nitinol hypotube (e.g., tube 46) coupled to the polyimide shaft with a suitable adhesive (e.g, LOCTITE® adhesive, which includes cyanoacrylates) and a piece of nitinol hypotube fashioned in the desired shape and welded (e.g, laser welded) to the short piece of nitinol hypotube. Stent-retention element 70 may include an intertwined stainless steel wire (used as proximal portion 72) that is covered with a material such as nylon, FEP (fluorinated ethylene propylene) tubing, or PET (polyester) tubing, and distal portion 71 may be made from stainless steel hypotube. Furthermore, steps may be taken to reduce the friction between the parts that contact or may contact either other during use of the present devices, such as contact between the stent and the outer sheath.

The present devices may be used to deliver self-expending stents that are woven, including stents woven from multiple strands, such as wires. Some examples of weaving techniques that may be used include those in U.S. Pat. Nos. 6,792,979 and 7,048,014, which are incorporated by reference. The strands of a woven stent may terminate in strand ends (e.g, wire ends) that are then joined together using small segments of material, such as nitinol hypotube, when the stent strands are wires made from nitinol. The stent may be passivated through any suitable technique in order to remove the oxide layer from the stent surface that can be formed during any heat treating and annealing, thus improving the surface finish and corrosion resistance of the stent material. Suitable stent creation techniques for stents that may be used with the present devices (including the strand crossings that may be engaged by stent-engaging element 45) are set forth in U.S. patent application Ser. No. 11/876,666, which is incorporated by reference.

It should be understood that the present devices and methods are not intended to be limited to the particular forms disclosed. Rather, they are to cover all modifications, equivalents, and alternatives falling within the scope of the claims. For example, while the embodiments of the present devices shown in the figures included a stent-engaging element and a user-actuatable element that moved the same distances in response to operator input, other embodiments of the present devices could include gears or other mechanisms that create a ratio between the distance that the user-actuatable element moves and the resulting distance that the stent-engaging element moves that is not 1:1 (such that the reciprocating element distance can be greater or less than the user-actuatable element distance). Furthermore, still other embodiments may employ other structures for achieving periodic engagement of a stent in order to advance it distally, such as a through a squeeze-trigger mechanism similar to the one shown in U.S. Pat. No. 5,968,052, which is incorporated by reference, or in U.S. Pat. No. 6,514,261, which is incorporated by reference, or through a stent-engaging element that rotates rather than translates and that possesses a cam portion configured to engage the stent during part of a given rotation and not engage the stent during another part of that rotation. Furthermore, still other embodiments may employ other forms of reciprocating movement of a stent-engaging element (such as stent-engaging element 45), such as through another form of operator input like a rotational user-actuatable input (rather than a translation input, as is shown in the figures) coupled to the stent-engaging element via a cam.

The claims are not to be interpreted as including means-plus- or step-plus-function limitations, unless such a limitation is explicitly recited in a given claim using the phrase(s) "means for" or "step for," respectively.

We claim:

1. A device comprising:
   an outer sheath;
   a stent disposed within the outer sheath, the stent having a distal end and a proximal end;
   a stent-engaging element positioned at least partially within a lumen of the stent; and
   a stent-retention element configured to contact the proximal end of the stent;
   a handle coupled to the outer sheath such that the outer sheath cannot move relative to the handle;
   a user-actuatable element movable along the handle, the user-actuatable element being coupled to the stent-engaging element;
   a stopper biased to a first position that restricts distal advancement of the user-actuatable element, the stopper comprising a passageway, wherein the stopper has a second position that allows the user-actuatable element to pass through the passageway;
   wherein the device is configured such that:
   the stent-engaging element is configured to operate in a reciprocating manner to engage and advance the stent distally at least partially out of the outer sheath; and
   the stent-retention element will stay in contact with the stent during proximal movement of the stent-engaging element provided that the proximal end of the stent is disposed within the outer sheath and will cease contact when the proximal end of the stent is advanced outside of the outer sheath.

2. The device of claim 1, wherein the user-actuatable element is coupled to the stent-engaging element by an element having a passageway.

3. The device of claim 2, further comprising:
   an inner element having a portion positioned within the element having a passageway, the inner element being configured to accept a guidewire.

4. The device of claim 1, where the user-actuatable element is movable within a slot of the handle.

5. The device of claim 1, where the stent has a deployment length, the outer sheath has a distal end, and the device further comprises:
   a marker coupled to the outer sheath and spaced apart from the outer sheath's distal end by a distance corresponding substantially to the deployment length of the stent.

6. The device of claim 1, further comprising:
   a side port coupled to the handle.

7. The device of claim 1, further comprising
   an element that can be coupled to the outside of the outer sheath, the element being configured to interface with a hemostasis valve of an introducer.

8. The device of claim 1, further comprising:
   a Y-adapter coupled to the handle;
   where the stent-retention element includes a distal portion and a stent-retention line extending from outside a branch of the Y-adapter and through the branch, the handle, and a portion of the outer sheath to the distal portion of the stent-retention element.

9. The device of claim 1, where the stent is woven, and the stent-engaging element is configured so as to (a) engage wire intersections on opposing sides of the stent when driving the stent distally, and (b) fold inwardly and slide proximally within the stent's lumen.

10. The device of claim 1, wherein the stent-engaging element is shaped like a shovel.

11. The device of claim 1, wherein the stent-engaging element is configured to operate in the reciprocating manner without a mechanized concomitant withdrawal of the outer sheath.

12. The device of claim 1, wherein the stopper in the second position allows the user-actuatable element to travel a full length of a slot.

13. A device comprising:
    an outer sheath;
    a handle coupled to the outer sheath such that the outer sheath cannot move relative to the handle, the handle having a proximal end and a user-actuatable element constrained by a length of a slot;
    a stent disposed within the outer sheath, the stent having a distal end and a proximal end;
    a stent-engaging element coupled to the user-actuatable element and configured to engage the stent between the distal and proximal ends of the stent; and
    a stopper comprising a passageway, the stopper biased to a first position that restricts distal advancement of the user-actuatable element, wherein the stopper has a second position that allows the user-actuatable element to pass through the passageway to travel a full length of the slot,
    wherein distal and proximal movement of the user-actuatable element advances the stent distally out of the outer sheath through multiple engagements of the stent by the stent-engaging element,
    wherein each engagement occurs between the proximal and distal ends of the stent,
    wherein distal movement of the user-actuatable element drives the stent distally without a mechanized concomitant withdrawal of the outer sheath, and
    wherein proximal movement of the user-actuatable element does not drive the stent distally; and
    the user's proximal-most point of contact with the device that causes each engagement is located at or distal of the proximal end of the handle.

14. The device of claim 13, wherein the user-actuatable element is coupled to the stent-engaging element by an element having a passageway.

15. The device of claim 14, further comprising:
    an inner element having a portion positioned within the element having a passageway, the inner element being configured to accept a guidewire.

16. The device of claim 14, further comprising:
    a side port coupled to the handle.

17. The device of claim 13, where the stent has a deployment length, the outer sheath has a distal end, and the device further comprises:
    a marker coupled to the outer sheath and spaced apart from the outer sheath's distal end by a distance corresponding substantially to the deployment length of the stent.

18. The device of claim 13, further comprising
    an element that can be coupled to the outside of the outer sheath, the element being configured to interface with a hemostasis valve of an introducer.

19. The device of claim 13, further comprising:
    a Y-adapter coupled to the handle; and
    a stent-retention element coupled to the proximal end of the stent;

where the stent-retention element includes a distal portion and a stent-retention line extending from outside a branch of the Y-adapter and through the branch, the handle, and a portion of the outer sheath to the distal portion of the stent-retention element.

20. The device of claim 13, further comprising:
a stent-retention element coupled to the proximal end of the stent.

21. The device of claim 13, where the stent is woven, and the stent-engaging element is configured so as to (a) engage wire intersections on opposing sides of the stent when driving the stent distally, and (b) fold inwardly and slide proximally within the stent's lumen.

22. The device of claim 13, wherein the stent-engaging element is shaped like a shovel.

23. A device comprising:
an outer sheath;
a handle coupled to the outer sheath such that the outer sheath cannot move relative to the handle, the handle having a proximal end;
a stent disposed within the outer sheath, the stent having a lumen, a distal end and a proximal end;
a stent-engaging element positioned at least partially within the lumen of the stent, the stent-engaging element shaped like a shovel and configured to engage two intersections on opposing sides of the stent when driving the stent distally;
a user-actuatable element slidable along a slot of the handle; and
a stopper biased to a first position that restricts distal advancement of the user-actuatable element, the stopper comprising a passageway, the user-actuatable element movable along a portion of the slot when the stopper is in the first position, the portion less than a full length of the slot, and movable along the full length of the slot and through the passageway when the stopper is in a second position,
where the device is configured such that:
a user can advance the stent distally out of the outer sheath through at least two periods of engagement of the stent by the stent-engaging element that drive the stent distally and that are separated by a period of non-engagement that does not drive the stent distally; and
the user's proximal-most point of contact with the device that causes each period of engagement is located at or distal of the proximal end of the handle.

24. The device of claim 23, further comprising:
the user-actuatable element also being coupled to the stent-engaging element by an element having a passageway.

25. The device of claim 24, further comprising:
an inner element having a portion positioned within the element having a passageway, the inner element being configured to accept a guidewire.

26. The device of claim 23, where the stent has a deployment length, the outer sheath has a distal end, and the device further comprises:
a marker coupled to the outer sheath and spaced apart from the outer sheath's distal end by a distance corresponding substantially to the deployment length of the stent.

27. The device of claim 23, further comprising:
a side port coupled to the handle.

28. The device of claim 23, further comprising
an element that can be coupled to the outside of the outer sheath, the element being configured to interface with a hemostasis valve of an introducer.

29. The device of claim 23, further comprising:
a Y-adapter coupled to the handle; and
a stent-retention element coupled to the proximal end of the stent;
where the stent-retention element includes a distal portion and a stent-retention line extending from outside a branch of the Y-adapter and through the branch, the handle, and a portion of the outer sheath to the distal portion of the stent-retention element.

30. The device of claim 23, further comprising:
a stent-retention element coupled to the proximal end of the stent.

31. The device of claim 23, where the stent is woven, and the stent-engaging element is configured so as to fold inwardly and slide proximally within the stent's lumen.

32. The device of claim 23, wherein the shovel stent-engaging element includes a flex slot.

33. The device of claim 23, wherein the device is configured to advance the stent distally out of the outer sheath without a mechanized concomitant withdrawal of the outer sheath.

34. The device of claim 23, wherein the stopper in the second position allows the user-actuatable element to travel a full length of a slot.

35. A device comprising:
an outer sheath;
a stent disposed within the outer sheath, the stent having a lumen, a distal end and a proximal end;
an inner element positioned at least partially within the lumen of the stent, the inner element being configured to accept a guidewire; and
a stent-engaging element separate from the inner element and positioned at least partially within the lumen of the stent;
a handle coupled to the outer sheath such that the outer sheath cannot move relative to the handle;
a user-actuatable element movable along the handle, the user-actuatable element being coupled to the stent-engaging element;
a stopper biased to a first position that restricts distal advancement of the user-actuatable element, the stopper comprising a passageway, wherein the stopper has a second position that allows the user-actuatable element to pass through the passageway;
wherein the device is configured to distally drive the stent at least partially out of the outer sheath through at least two periods of engagement of the stent by the stent-engaging element that are separated by a period of non-engagement that does not drive the stent distally.

36. The device of claim 35, wherein the user-actuatable element is coupled to the stent-engaging element by an element having a passageway.

37. The device of claim 35, where the user-actuatable element is a movable within a slot of the handle.

38. The device of claim 35, where the stent has a deployment length, the outer sheath has a distal end, and the device further comprises:
a marker coupled to the outer sheath and spaced apart from the outer sheath's distal end by a distance corresponding substantially to the deployment length of the stent.

39. The device of claim 35, further comprising:
a side port coupled to the handle.

40. The device of claim 35, further comprising
an element that can be coupled to the outside of the outer sheath, the element being configured to interface with a hemostasis valve of an introducer.

41. The device of claim 35, further comprising:
a Y-adapter coupled to the handle; and
a stent-retention element coupled to the proximal end of the stent;
where the stent-retention element includes a distal portion and a stent-retention line extending from outside a branch of the Y-adapter and through the branch, the handle, and a portion of the outer sheath to the distal portion of the stent-retention element.

42. The device of claim 35, further comprising:
a stent-retention element coupled to the proximal end of the stent.

43. The device of claim 35, where the stent-engaging element is also configured to fold inwardly and slide proximally within the stent's lumen.

44. The device of claim 35, wherein the device is configured to distally drive the stent at least partially out of the sheath without a mechanized concomitant withdrawal of the outer sheath.

45. The device of claim 35, wherein the stent-engaging element is shaped like a shovel.

46. The device of claim 35, wherein the stent-engaging element is configured to engage two intersections on opposing sides of the stent.

47. The device of claim 35, wherein the stopper in the second position allows the user-actuatable element to travel a full length of a slot.

48. A stent advancement method comprising:
distally driving a stent out of a sheath and into a tubular structure by engaging the stent between its distal and proximal ends with a stent-engaging element a multiple number of engagements, wherein the multiple number of engagements are separated by a period of non-engagement, and wherein during each of the multiple number of engagements, the stent-engaging element moves from a first position to a second position distal to the first position; and
engaging the stent at its proximal end with a stent-retention element that is positioned within the sheath,
wherein an operator accomplishes the driving of the stent by moving a user-actuatable element with the operator's thumb,
wherein the user-actuatable element is constrained by a traversable length of a slot, and
wherein moving a stopper from a first position to a second position to a second position changes the traversable length of the slot.

49. The stent advancement method of claim 48, where the tubular structure is animal tissue.

50. The stent advancement method of claim 49, where the stent-retention element includes a stent-retention line, and the method further comprises:
after the stent is partially-driven out of the sheath, withdrawing the stent back into the sheath by moving the stent-retention line.

51. The stent advancement method of claim 50, where an operator accomplishes the driving of the stent by moving a user-actuatable element with the operator's thumb.

52. The stent advancement method of claim 51, where the stent is woven, the stent-engaging element engages multiple wire intersections of the stent and moves distally during the engagements that drive the stent, and the stent-engaging element slides proximally within the stent's lumen during the period of non-engagement.

53. The stent advancement method of claim 48, where the tubular structure is not part of an animal.

54. The stent advancement method of claim 53, where the stent-retention element includes a stent-retention line, and the method further comprises:
after the stent is partially-driven out of the sheath, withdrawing the stent back into the sheath by moving the stent-retention line.

55. The stent advancement method of claim 48, where the stent is woven, the stent-engaging element engages multiple wire intersections of the stent and moves distally during the engagements that drive the stent, and the stent-engaging element slides proximally within the stent's lumen during the period of non-engagement.

56. The stent advancement method of claim 48, wherein distally driving the stent out of the sheath occurs without a mechanized concomitant withdrawal of the outer sheath.

57. The stent advancement method of claim 48, wherein, during the period of non-engagement, the stent-engagement element folds inwardly and slides proximally.

58. The stent advancement of claim 48, wherein, during the multiple number of engagements, the stent-engaging element engages two intersections on opposing sides of the stent.

59. The stent advancement method of claim 48, wherein the stent-engagement element is shaped like a shovel.

60. A device comprising:
an outer sheath;
a handle coupled to the outer sheath, the outer sheath being stationary relative to the handle, the handle including a user-actuatable element coupled to a pusher, the user-actuatable element movable along a slot of the handle;
a stopper comprising a passageway, the stopper rotatable from a first position in which the passageway is not aligned with the slot to a second position in which the passageway is aligned with the slot;
a stent disposed within the outer sheath; and
a stent-engaging element disposed within the outer sheath and coupled to the pusher;
wherein the stent is distally driveable out of the outer sheath through at least two periods of engagement of the stent by the stent-engaging element, each said period of engagement configured to drive the stent distally without a mechanized concomitant withdrawal of the outer sheath and each said period of engagement separated by a period of non-engagement of the stent by the stent-engaging element that is configured to not drive the stent distally.

61. The device of claim 60, wherein the stent has a distal end, a proximal end, and a lumen extending between the distal end and the proximal end, and wherein the stent-engaging element is positioned at least partially within the lumen of the stent.

62. The device of claim 60, wherein the pusher includes a passageway.

63. The device of claim 62, wherein the passageway is configured to accept a guidewire.

64. The device of claim 60, wherein, in the second position, the stopper allows the user-actuatable element to travel a full length of a slot and wherein the stopper is biased in the first position.

65. The device of claim 60, wherein the stent has a proximal end and wherein the device further comprises a stent-retention element engaging the proximal end of the stent while the proximal end of the stent is in the outer sheath.

66. The device of claim 60, wherein the stent comprises a plurality of woven wires.

67. The device of claim 66, wherein the stent-engaging element is configured to (a) engage wire intersections during each said period of engagement, and (b) fold inwardly and slide proximally during each said period of non-engagement.

68. The device of claim 60, wherein the handle has a proximal end and wherein a proximal-most point of contact of a user with the device that causes each said period of engagement is located at or distal of the proximal end of the handle.

69. The device of claim 60, wherein the stent-engaging element is shaped like a shovel or scoop.

70. A stent advancement method comprising:
moving a user-actuatable element from a first position in a slot of a handle to a second position in the slot of the handle, the user-actuatable element coupled to a stent-engaging element, wherein during moving the user-actuatable element from the first position to the second position, the stent-engaging element engages a stent between distal and proximal ends of the stent to distally drive a first portion of the stent out of a sheath while a second portion of the stent remains within the sheath;
after moving the user-actuatable element from the first position to the second position, moving the user-actuatable element from the second position to the first position, wherein during moving the user-actuatable element from the second position to the first position, the stent-engaging element folds inwardly and slides proximally within the stent;
after moving the user-actuatable element from the second position to the first position, second moving the user-actuatable element from the first position to the second position, wherein during second moving the user-actuatable element from the first position to the second position, the stent-engaging element engages the stent between the distal and proximal ends of the stent to drive the second portion of the stent at least partially out of the sheath;
after second moving the user-actuatable element from the first position to the second position, rotating a stopper to increase a traversable length of the slot of the handle by the user-actuatable element; and
moving the user-actuatable element to a third position distal to the second position, wherein during moving the user-actuatable element to the third position, the stent-engaging element extends out of the sheath.

71. The method of claim 70, wherein moving the user-actuatable element from the first position to the second position occurs without a mechanized concomitant withdrawal of an outer sheath.

72. The method of claim 70, wherein the user-actuatable element is biased toward the second position in the slot of the handle.

73. The method of claim 70, further comprising engaging a proximal end of the stent with a stent-retention element.

74. The method of claim 70, wherein the stent is woven and the stent-engaging element is configured to engage two intersections on opposing sides of the stent.

75. The method of claim 70, wherein the stent-engaging element is shaped like a shovel.

\* \* \* \* \*

UNITED STATES PATENT AND TRADEMARK OFFICE
CERTIFICATE OF CORRECTION

| | | |
|---|---|---|
| PATENT NO. | : 8,876,881 B2 | Page 1 of 1 |
| APPLICATION NO. | : 11/876764 | |
| DATED | : November 4, 2014 | |
| INVENTOR(S) | : Jeffery Sheldon et al. | |

It is certified that error appears in the above-identified patent and that said Letters Patent is hereby corrected as shown below:

In the Specification

In Column 2, Line 44, change "actuable" to --actuatable--.

In Column 7, Line 1, change "concomittant" to --concomitant--.

In Column 7, Line 39, change "concomittant" to --concomitant--.

In Column 9, Line 20, change "drawing" to --withdrawing--.

In Column 10, Line 43, change "concomittantly" to --concomitantly--.

In Column 11, Line 35, change "mpg," to --.mpg,--.

In the Claims

In Column 16, Line 17, in Claim 32, change "the shovel" to --the--.

In Column 18, Line 20, in Claim 58, change "advancement" to --advancement method--.

Signed and Sealed this
Twenty-ninth Day of September, 2015

Michelle K. Lee
*Director of the United States Patent and Trademark Office*